(12) United States Patent
Lin et al.

(10) Patent No.: US 8,084,431 B2
(45) Date of Patent: Dec. 27, 2011

(54) METHOD FOR INHIBITING ACTIVATION OF MACROPHAGES, INHIBITING FORMATION OF OSTEOCLASTS, INHIBITING FUNCTION OF OSTEOCLASTS, AND/OR ACTIVATING OSTEOBLASTS

(75) Inventors: Wen-Chuan Lin, Taichung (TW); Jin-Bin Wu, Taichung (TW); Hung-Bo Hsiao, Taichung (TW); Hui-Ya Ho, Taichung (TW)

(73) Assignee: China Medical University, Taichung (TW)

( * ) Notice: Subject to any disclaimer, the term of this patent is extended or adjusted under 35 U.S.C. 154(b) by 362 days.

(21) Appl. No.: 12/454,001

(22) Filed: May 11, 2009

(65) Prior Publication Data

US 2009/0306199 A1     Dec. 10, 2009

(30) Foreign Application Priority Data

Dec. 31, 2008   (TW) .................... 97151694 A

(51) Int. Cl.
*A61K 31/70*          (2006.01)
(52) U.S. Cl. .......................................... 514/27
(58) Field of Classification Search ..................... 514/27
See application file for complete search history.

(56) References Cited

FOREIGN PATENT DOCUMENTS

JP          10-056875 A          3/1998

OTHER PUBLICATIONS

Chia-Tzu Tsai, "Protective effect of kinsenoside on liver injury induced by carbon tetrachloride in mice: Possible involvement of thre Pupffer cell inactivation" (Jul. 2008).
Fujiwara N. Kobayashi K. 2005. Macrophage and inflammation. *Curr Drug Targets* 4, 281-286.
Naito M. 2008. Macrophage differentiation and function in health and disease. *Pathol Int* 58, 143-156.
Shih CC, Wu YW, Lin WC. 2001. Ameliorative effects of *Anoectochilus formosanus* extract on osteopenia in overiectomized rats. J Ethnopharmacol 77, 233-238.
Masuda K, Ikeuchi M, koyama T, Yamaguchi K, Woo JT, Nishimura T, Yazawa K. 2008. Suppressive effects of *Anoectochilus formosanus* extract on osteoclast formation in vitro and bone resorption in vivo. J Bone Miner Metab 26, 123-129.
Shiau YJ, Sagare AP, Chen UC, Yang SR, Tsay HS. 2002. Conservation of *Anoectochilus formosanus* HAYATA by artificial cross-pollination and in vitro culture of seeds. Bot Bull Acad Sin 43: 123-130.
Cavaillon JM. Adib-Conquy M. 2005. Monocytes/macrophages and sepsis. Crit Care Med 33, S506-S509.
Ito A, Kasai R, Yamasaki K, Sugimoto H, 1993, Aliphatic and aromatic glucosides from *Anoectochilus koshunesis*, Phytochemistry 33: 1133-1137.
Du XM, Yoshizawa T, Shoyama Y. 1998, Butanolic acid glucoside composition of whole body and in vitro plantlets of *Anoectochilus formosanus*, Phytochemistry 49: 1925-1928.
Zhang X, Lin ZY, Huang HH, Chen QH, 2004, Novel total synthesis of kinsenoside, Chinese Journal of Synthetic Chemistry 12, 317-318.

*Primary Examiner* — Raymond Henley, III
(74) *Attorney, Agent, or Firm* — Patterson Thuente Christensen Pedersen, P.A.

(57) ABSTRACT

A method for inhibiting the activation of macrophages, inhibiting the formation of osteoclasts, inhibiting the function of osteoclasts, and/or activating osteoblasts in a mammal is provided. The method comprises the administration of an effective amount of kinsenoside of formula (I) or a pharmaceutically acceptable salt or ester thereof to the mammal:

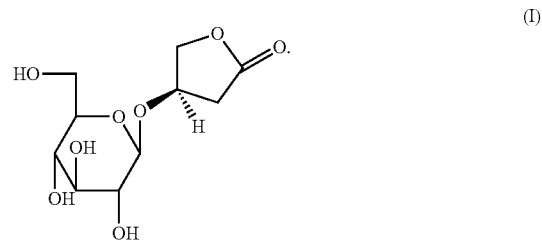

(I)

12 Claims, 12 Drawing Sheets
(3 of 12 Drawing Sheet(s) Filed in Color)

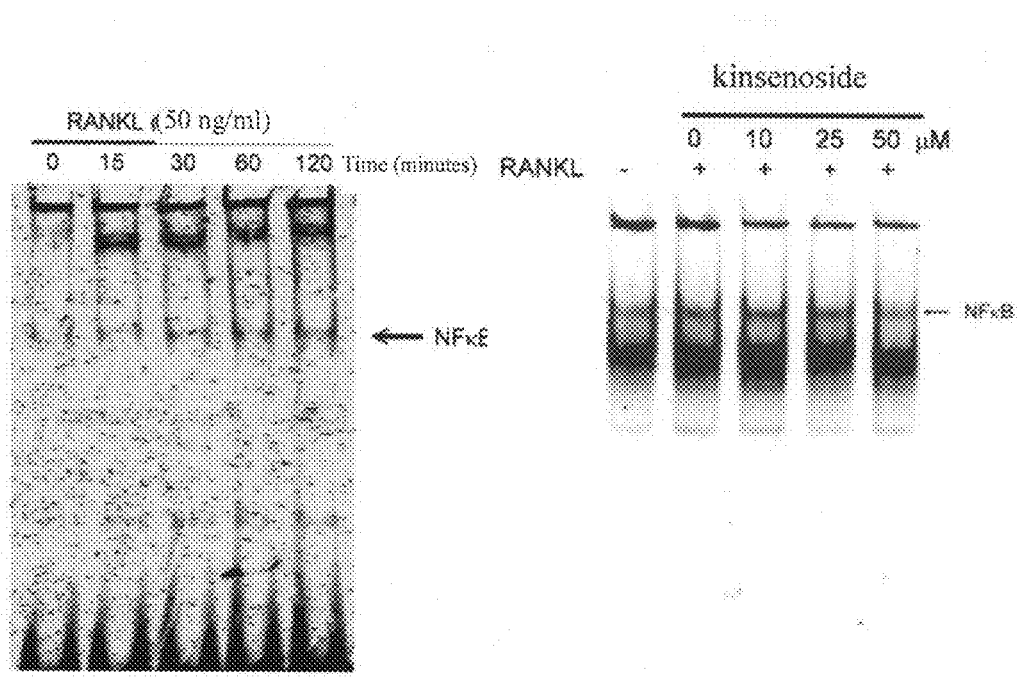
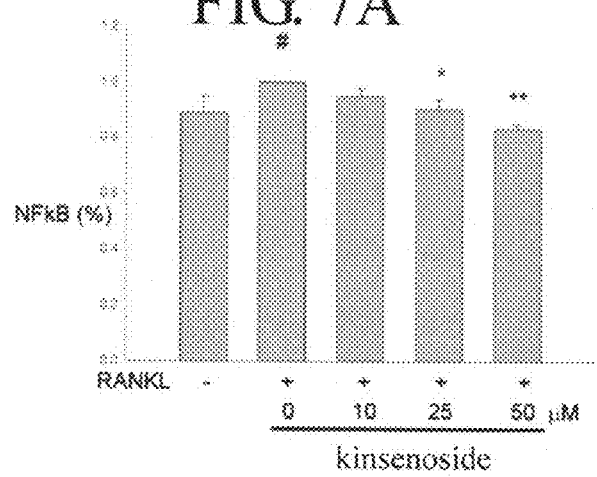
FIG. 7A
FIG. 7B
FIG. 7C

_US 8,084,431 B2_

METHOD FOR INHIBITING ACTIVATION OF MACROPHAGES, INHIBITING FORMATION OF OSTEOCLASTS, INHIBITING FUNCTION OF OSTEOCLASTS, AND/OR ACTIVATING OSTEOBLASTS

This application claims priority to Taiwan Patent Application No. 097151694 filed on Dec. 31, 2008.

CROSS-REFERENCES TO RELATED APPLICATIONS

Not applicable.

BACKGROUND OF THE INVENTION

1. Field of the Invention

The present invention relates to the uses of kinsenoside for inhibiting the activation of macrophages, inhibiting the formation of osteoclasts, inhibiting the function of osteoclasts, and/or activating osteoblasts.

2. Descriptions of the Related Art

Bones mainly consist of organic components (e.g. collagenic fibers and mucopolysaccharides), inorganic components (calcium salts and phosphoric salts), water, etc. Bone tissue is in a dynamic equilibrium state. Bone formation and bone resorption, both of which make up the process of bone remodeling, occur in the bone tissue continuously, and they not only can cure slight trauma, but can also enhance the pressure resistance of bones. In addition, the bone formation includes the formation of a new bone matrix and the mineralization of bones.

The bone modeling process relies on the cooperation of two different kinds of cells, osteoblasts and osteoclasts, responsible for the bone formation and the bone resorption, respectively. If any mistake occurs in the coordination between the two cells, it will lead to an imbalance of bone remodeling. For example, if the level of bone resorption is greater than that of bone formation, osteoporosis, commonly seen in clinical medicine (especially postmenopausal women), will take place. On the contrary (i.e. the level of the bone resorption is less than that of the bone formation) is rare, and it may cause an abnormal increase of bone tissue.

Currently, there are about two hundred millions of females with osteoporosis. In 2003, the global market for osteoporosis and hormone supplement therapy for osteoporosis is worth about 8.3 billions USD, and is predicted to reach 17.9 billions USD in 2014. According to mechanisms, pharmaceuticals for osteoporosis can be generally classified into four groups. The first group inhibits the bone resorption, one example of which is diphosphates. The second group stimulates the bone formation, one example of which is parathyroid hormone. The third group inhibits the release of calcium from bones, one example of which is estrogen. The fourth group stimulates the small intestine to absorb calcium, one example of which is Vitamin D. However, diphosphates may bring strong side effects (such as headaches, nausea, vomiting, diarrhea, fever, renal failure, oesophagitis, mandible necrosis, etc). The parathyroid hormone may cause uncomfortableness (such as headaches and nausea). The estrogen has a risk of causing cancer. In addition, the effect of using Vitamin D to enhance the absorption of calcium to improve osteoporosis is quite limited. Therefore, a substance or a pharmaceutical composition that can cure osteoporosis efficiently and with low side effects is still needed.

Macrophages present various differentiated cell forms in different tissues, for instance, Kupffer cells in the liver or microglials in the brain. In the bone tissue, macrophages present a differentiated form as osteoclasts, which maintain a dynamic equilibrium state with osteoblasts.

In the immunological defense mechanism of humans, macrophages in the blood are the first line of defense, and thus, play a very important role in the inflammatory reaction. Specifically, when contacting pathogens, macrophages are activated to trigger the ability for destroying pathogens, and meanwhile secrete cytokines, for example tumor necrosis factor-α (TNF-α) and interleukin-6 (IL-6), that stimulate the inflammatory reaction. Hence, if the stimulation from pathogens is too strong, or macrophages release too much cytokines within a short period of time, septic shock may arise.

During the inflammatory process, macrophages not only release cytokines, but also present antigens. More specifically, the action of presenting antigens of macrophages may influence the differentiation of T cells, and further influence the generation of B cells and antibodies. B cells and antibodies can also destroy pathogens. Therefore, besides being the first immunological response, macrophages play a role in immunological modulation (see Fuijwara N. Kobayashi K. Macrophage and inflammation. _Curr Drug Targets_ 4, 281-286).

Present studies show that nearly all chronic diseases are relevant to the inflammatory reaction, such as cancers, rheumatic arthritis, etc. In other words, macrophages participate in the morbific mechanisms of these diseases (see Naito M. 2008. Macrophage differentiation and function in health and disease. _Pathol Int_ 58, 143-156).

For rheumatic arthritis, macrophages play an important role in the pathology of this disease. Generally speaking, rheumatic arthritis may activate macrophages to release cytokines, and thus stimulates chronic inflammation. In addition, various kinds of inflammatory cells exist in the joint synovial fluid, and cytokines and growth factors released from the inflammatory cells can make macrophages differentiate into osteoclasts, thus causing damage to joint bones. The main pharmaceutical for rheumatic arthritis currently is steroids. However, steroids have many side effects, such as edema, osteoporosis, etc. Accordingly, a substance or a pharmaceutical composition that can cure rheumatic arthritis efficiently with low side effects is still highly demanded.

_Anoectochilus_ spp. belongs to orchidaceae, and it is believed that _Anoectochilus formosanus_ Hayata has the broad effects of decreasing blood pressure, reducing blood sugar, protecting the liver, anti-inflammation, modulating immune system, and so on. Thus, _Anoectochilus formosanus_ Hayata is also called "the king of drugs" or "the tiger of drugs." Furthermore, it has been confirmed by documents that the crude extract of _Anoectochilus formosanus_ Hayata has the pharmacological effect of anti-osteoporosis (see Shih C C, Wu Y W, Lin W C. 2001. Ameliorative effects of _Anoectochilus formosanus_ extract on osteopenia in overiectomized rats. _J Ethnopharmacol_ 77, 233-238 and Masuda K, Ikeuchi M, koyama T, Yamaguchi K, Woo J T, Nishimura T, Yazawa K. 2008. Suppressive effects of _Anoectochilus formosanus_ extract on osteoclast formation in vitro and bone resorption in vivo. _J Bone Miner Metab_ 26, 123-129).

Nevertheless, the active component for the anti-inflammation and anti-osteoporosis effects of _Anoectochilus formosanus_ Hayata remains unclear at present, and the optimization of drug efficiency and the pharmacological study are limited accordingly. Moreover, because the traditional suckering proliferation method is quite slow, and the consumption due to collection is not limited, the number of _Anoectochilus formosanus_ Hayata in its natural habitat has decreased dramatically. Although the industry has actively studied cultural methods for *Anoectochilus formosanus* Hayata (e.g., a vegetative propagation method using the tissue culture of *Anoectochilus formosanus* Hayata, which can be seen in Shiau Y J, Sagare A P, Chen U C, Yang S R, Tsay H S. 2002. Conservation of *Anoectochilus formosanus* HAYATA by artificial cross-pollination and in vitro culture of seeds. *Bot Bull Acad Sin* 43: 123-130, an improved seedling root culture method disclosed in JP 10-056875 A, etc), the number of *Anoectochilus formosanus* Hayata that can be provided is still restricted by the reproduction/culture speed. Thus, if the active component for anti-inflammation and anti-osteoporosis effects provided by *Anoectochilus formosanus* Hayata can be obtained, a pharmaceutical composition comprising the active component can be provided and produced in large scale by an artificial synthesis process.

The present invention is the investigation for the above requirements. The inventors of the present invention discovered the main active compound for anti-inflammation and anti-osteoporosis in *Anoectochilus formosanus* Hayata through related in vivo and in vitro experiments. The active compound has the functions of stimulating the bone formation and inhibiting the bone resorption, and also has the effect of inhibiting the activation of macrophages.

SUMMARY OF THE INVENTION

One objective of this invention is to provide a method for inhibiting the activation of macrophages, inhibiting the function of osteoclasts, inhibiting the formation of osteoclasts, and/or activating osteoblasts in a mammal comprising the administration of an effective amount of a compound of formula (I) or a pharmaceutically acceptable salt or ester thereof to the mammal:

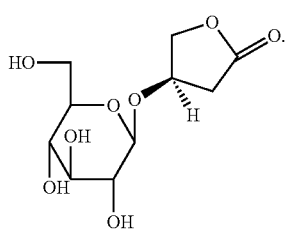

(I)

The detailed technology and preferred embodiments implemented for the subject invention are described in the following paragraphs accompanying the appended drawings for people skilled in this field to well appreciate the features of the claimed invention.

The patent or application file contains at least one drawing executed in color. Copies of this patent with color drawing(s) will be provided by the Patent and Trademark Office upon request and payment of the necessary fee.

BRIEF DESCRIPTION OF THE DRAWINGS

FIG. 7A is a figure of Electrophoresis Mobility Shift Assay (EMSA) of NF-κB after using RANKL to activate macrophages RAW 264.7;

FIG. 7B is a figure of EMSA of NF-κB after the administration of kinsenoside to macrophages RAW 264.7;

FIG. 7C is a statistic column diagram of NF-κB entering into nuclei after the administration of kinsenoside to macrophages RAW 264.7;

DESCRIPTION OF THE PREFERRED EMBODIMENT

Figure 1:
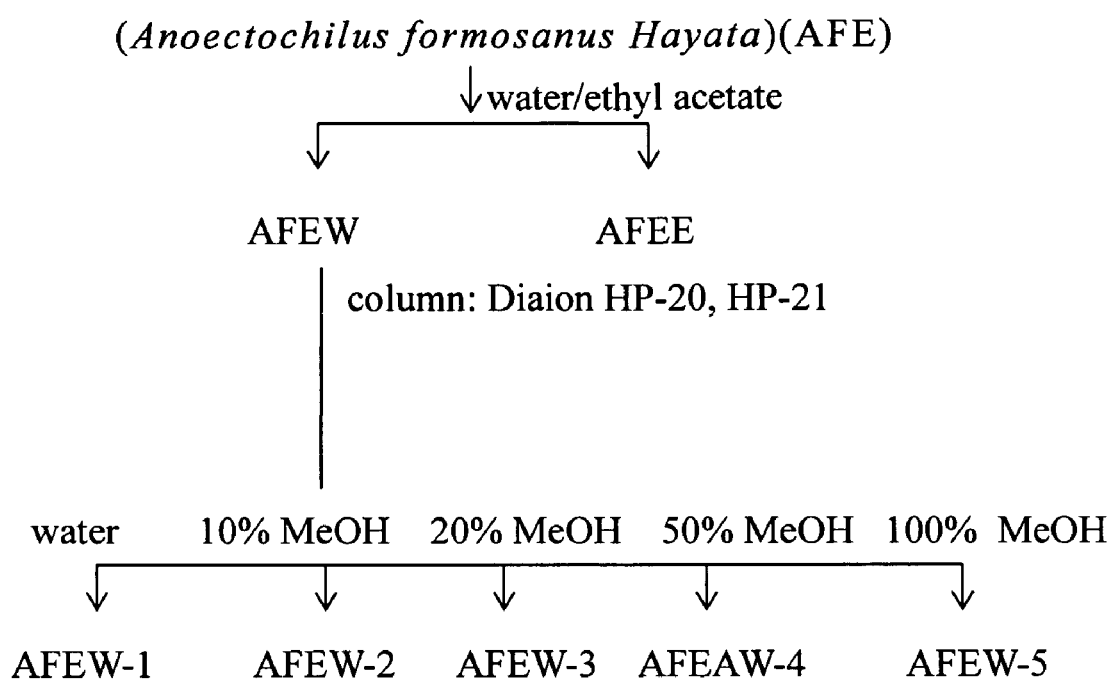
FIG. 1 is a flow chart for extracting and isolating kinsenoside.

In reference to the aforesaid descriptions, it is known that the crude extract of *Anoectochilus formosanus* Hayata has the functions of anti-inflammation and anti-osteoporosis; however, the effective component therein remains unclear. The inventors of the present invention carried out many times of cell experiments in vitro and many times of animal experiments in vivo, and discovered that the compound of formula (I) is the main active component with the functions of inhibiting the activation of macrophages, inhibiting the formation of osteoclasts, inhibiting the function of osteoclasts, and/or activating osteoblasts in *Anoectochilus formosanus* Hayata:

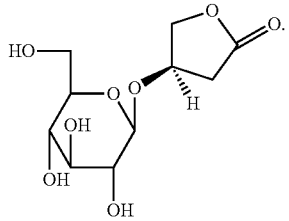
(I)

The compound of formula (I) is the so-called "kinsenoside," and the compound of formula (I) will be represented as "kinsenoside" hereinafter.

It is believed that osteoporosis is caused by the imbalance between the bone formation and the bone resorption. Osteoblasts in bones are responsible for the bone formation, whereas osteoclasts in bones are responsible for the bone resorption. Specifically, one of the causes for osteoporosis is that the number of osteoclasts in bones is much greater than normal, or the bone resorption rate caused by osteoclasts is too high, and thus, bones lose significant calcium that results in the decrease of bone density. Therefore, if the function of osteoclasts (i.e., the bone resorption) and/or the formation of osteoclasts (which can be derived from macrophages) can be inhibited, bone resorption can be controlled to further prevent or improve osteoporosis. Moreover, another cause for osteoporosis is that the bone formation effect of osteoblasts in bones is insufficient. Hence, if osteoblasts can be activated to stimulate the bone formation, calcium in bones can be increased to further prevent or improve osteoporosis.

As shown in the following examples, the inventors of the present invention found that kinsenoside has the effects of inhibiting the function of osteoclasts and inhibiting the formation of osteoclasts, and thus kinsenoside may alleviate/inhibit the bone resorption. Furthermore, the inventors of the present invention found that kinsenoside also has the effect of activating osteoblasts, and thus kinsenoside may stimulate bone formation. Surprisingly, kinsenoside is capable of (1) inhibiting the function of osteoclasts, (2) inhibiting the formation of osteoclasts, and (3) activating osteoblasts, and therefore, it is apparent that kinsenoside can provide a satisfactory effect in terms of the prevention and treatment of osteoporosis.

Accordingly, the present invention relates to a method for inhibiting the function of osteoclasts, inhibiting the formation of osteoclasts, and/or activating osteoblasts in a mammal, and especially for anti-osteoporosis. The method comprises administrating an effective amount of kinsenoside or a pharmaceutically acceptable salt or ester thereof to the mammal. In this text, the term "anti-osteoporosis" covers the prevention of osteoporosis, the improvement in osteoporosis, and the treatment of osteoporosis.

In addition, as described above, because kinsenoside has the effect of activating osteoclasts, the method of the present invention is also useful for bone formation.

In another aspect, the inventors of the present invention discovered that kinsenoside can not only inhibit the function/formation of osteoclasts and activate osteoblasts, but can also inhibit the activation of macrophages. Relevant researches have revealed that lipopolysaccharides (LPS), a component of the cell wall of gram-negative bacteria, may induce the activity of macrophages (see Cavaillon J M. Adib-Conquy M. 2005. Monocytes/macrophages and sepsis. *Crit Care Med* 33, S506-S509). As shown in the following examples, kinsenoside can inhibit lipopolysaccharides' ability to activate macrophages.

As described above, while destroying pathogens, macrophages secret cytokines that stimulate the inflammatory reaction. Thus, macrophages play an important role in the inflammatory reaction. Seeing that kinsenoside can inhibit the activation of macrophages (i.e., kinsenoside can inhibit the secretion of cytokines stimulating the inflammatory reaction from macrophages) to achieve the anti-inflammation effect, the method of the present invention can inhibit the activation of macrophages in a mammal, and can especially be used for anti-inflammation. The method comprises administrating an effective amount of kinsenoside or a pharmaceutically acceptable salt or ester thereof to the mammal. In this text, the term "anti-inflammation" covers the prevention of inflammation, the improvement in inflammation, and the treatment of inflammation.

In one embodiment of the present invention, the method of the present invention is especially suitable for treating the inflammatory reaction of arthritis. Specifically, since a great number of macrophages aggregates in the synovial fluid of joints at the early stage of arthritis, cytokines released by macrophages may stimulate the inflammatory reaction, thus causing injury to cartilages. In addition, at the later stage of arthritis, macrophages are activated to differentiate into osteoclasts, and then bone resorption occurs, which leads to injury to the joints. In other words, in the treatment of arthritis, inhibiting the activation of macrophages is a key step. Hence, kinsenoside can be used to prevent or treat any kinds of arthritis, such as rheumatoid arthritis, gouty arthritis, bacterial arthritis, degenerative arthritis, ankylosing arthritis, osteoarthritis, etc.

Therefore, one aspect of the present invention is to provide a method for inhibiting the activation of macrophages, inhibiting the formation of osteoclasts, inhibiting the function of osteoclasts, and/or activating osteoblasts in a mammal comprising the administration of an effective amount of kinsenoside or a pharmaceutically acceptable salt or ester thereof to the mammal. According to the method of the present invention, the effective amount of kinsenoside or a pharmaceutically acceptable salt or ester thereof is not critical, as long as the desired effects of inhibiting the activation of macrophages, inhibiting the formation of osteoclasts, inhibiting the function of osteoclasts, and/or activating osteoblasts can be provided. Herein, depending on the requirements of the treating target, the kinsenoside or its pharmaceutically acceptable salt or ester can be applied as a pharmaceutical composition with various administration frequencies, such as once a day, several times a day, or once for days, etc. For example, for anti-osteoporosis, the amount of kinsenoside or its pharmaceutically acceptable salt or ester contained in the pharmaceutical composition, calculated as kinsenoside, is about 4 wt % to about 8 wt %, preferably about 5 wt % to about 7 wt % based on the total weight of the composition. For anti-inflammation, the amount of kinsenoside or its pharmaceutically acceptable salt or ester contained in the pharmaceutical composition, calculated as kinsenoside, is about 7 wt % to about 13 wt %, preferably about 9 wt % to about 11 wt %, based on the total weight of the composition.

For anti-osteoporosis, in practice, the average dosage of kinsenoside or its pharmaceutically acceptable salt or ester is about 20 mg to about 200 mg per day per person (for an adult with the body weight of about 60 kg), preferably about 40 mg to about 150 mg per day per person, and particularly preferably about 60 mg to about 100 mg per day per person, wherein the dosage is based on kinsenoside. For anti-inflammation, the average dosage is about 30 mg to about 300 mg per day per person, preferably about 50 mg to about 200 mg per day per person, and particularly preferably about 70 mg to about 150 mg per day per person. However, in an acute situation (e.g., acute arthritis or serious osteoporosis), the dosage can be increased to several times or several tens of times, depending on the practical requirements.

Moreover, the pharmaceutical composition can be applied in any suitable ways. For instance, but not limited thereby, the pharmaceutical composition can be applied by oral administration, subcutemeous administration, or intravenous administration, etc. Kinsenoside or a pharmaceutically acceptable salt or ester thereof can be used individually or in combination with adjuvants, and can be used in both veterinary medicine and human medicine in practice.

Therefore, kinsenoside or its pharmaceutically acceptable salt or ester can be used to manufacture a medicament with any suitable forms for inhibiting the activation of macrophages, inhibiting the function of osteoclasts, inhibiting the formation of osteoclasts, and/or activating osteoblasts, especially for anti-osteoporosis and anti-inflammation (e.g., anti-arthritis). In terms of the manufacture of a medicament suitable for oral administration, kinsenoside or a pharmaceutically acceptable salt or ester thereof can be mixed with adjuvants that are suitable for oral administration and do not influence the activity of kinsenoside adversely. For example, the adjuvants can be a solvent, an oil solvent, a thinner, a stabilizer, an absorption-retarding reagent, a disintegrant, an emulsifier, a binder, a lubricant, a deliquescent, etc. For instance, the solvent can be water or a sucrose solution; the thinner can be lactose, starch, or microcrystalline cellulose; the absorption-retarding reagent can be chitosan or glycosaminoglycan; the lubricant can be magnesium carbonate; and the oil solvent can be plant oil or animal oil, such as olive oil, heliotrope oil, fish liver oil, etc. Herein, with a conventional method, the medicament can be made into a suitable oral administration form, such as a tablet, a capsule, a granule, a powder, a fluid extract, a solution, a syrup, a suspension, an emulsion, a tincture, etc.

As for a medicament suitable for a subcutemeous or intravenous administration form, depending on the requirements, kinsenoside or a pharmaceutically acceptable salt or ester thereof can be mixed with a material conventionally used for these forms (e.g., a hydrotropic agent, an emulsifier, or other adjuvants), to produce an intravenous injection, an emulsion intravenous injection, an injection, a powder injection, a suspension injection, a powder-suspension injection, etc. For instance, the solvent can be water, physiological solution of sodium chloride, alcohols (e.g., ethanol, propanol, glycerin, etc), sugar solution (e.g., glucose or mannitol solution), or a combination thereof.

Optionally, in addition to the above useful adjuvants, other additives, such as a flavoring agent, a toner, a coloring agent, and so on, can be added to enhance the sense of comfort for the mouth and visual feelings during the administration. A suitable dosage of a preservative, a conservative, an antiseptic, an anti-fungus reagent, and so on, also can be added to improve the storability of the resulting medicament.

In another aspect, the medicament may optionally combine one or more other active components to enhance the effect of the medicament or increase the flexibility and plasticity of the formulation. For example, other active components that can be incorporated with the medicament comprise pharmaceuticals for treating osteoporosis (e.g., alendronate, parathorine, estrogen, calcium compounds, or Vitamin D, etc), anti-arthritis pharmaceuticals (e.g., chondroitin or glucosamine), other active components, and so on, as long as the other active components have no adverse effects on kinsenoside.

Kinsenoside used in the method of the present invention can be provided from any natural or artificial synthesis sources. Preferably, kinsenoside is from *Anoectochilus* spp., especially from *Anoectochilus formosanus* Hayata. Herein, the isolation operation may be in combination with any suitable extraction methods, so as to acquire kinsenoside from *Anoectochilus* spp. Isolation methods can be seen in Ito A, Kasai R, Yamasaki K, Sugimoto H, 1993, Aliphatic and aromatic glucosides from *Anoectochilus koshunesis*, *Phytochemistry* 33: 1133-1137, and Du X M, Yoshizawa T, Shoyama Y. 1998, Butanolic acid glucoside composition of whole body and in vitro plantlets of *Anoectochilus formosanus*, *Phytochemistry* 49: 1925-1928, which are entirely incorporated hereinto as reference. In addition, kinsenoside also can be obtained by means of total synthesis, as disclosed in Zhang X, Lin Z Y, Huang H H, Chen Q H, 2004, Novel total synthesis of kinsenoside, *Chinese Journal of Synthetic Chemistry* 12, 317-318, which is entirely incorporated hereinto as reference.

Consequently, the present invention also provides a method for inhibiting the activation of macrophages, inhibiting the formation of osteoclasts, inhibiting the function of osteoclasts, and/or activating osteoblasts in a mammal comprising the administration of kinsenoside as an *Anoectochilus* spp. extract. Preferably, the *Anoectochilus* spp. extract is substantially free of ethyl acetate-philic components. In this text, the term "ethyl acetate-philic component" represents a component that can be removed by the partition with ethyl acetate as being dissolved in water. It is found that the ethyl acetate-philic component in the *Anoectochilus* spp. extract may cause injury to hepatocytes. With the removal of the ethyl acetate-philic component in the *Anoectochilus* spp. extract, potential damage caused by the use of the *Anoectochilus* spp. extract to an administration subject can be greatly reduced.

Preferably, the *Anoectochilus* spp. extract is an aqueous extract, and is free of ethyl acetate-philic components. The *Anoectochilus* spp. extract can be obtained by the following process. *Anoectochilus* spp. is first disintegrated into slurry in the water, and the slurry is filtrated to obtain an aqueous extract. Ethyl acetate is added into the aqueous extract, and then, the ethyl acetate partition is removed. Depending on the requirements, the operation of the partition with ethyl acetate can be repeated to reduce components soluble in ethyl acetate in the extract as much as possible.

In one embodiment of the present invention, the extract comprising kinsenoside can be obtained by the following method. First, *Anoectochilus formosanus* Hayata (10 kg) is first disintegrated in the water (100 L), and then, the resulting slurry is filtrated to acquire a solution (or cooking *Anoectochilus formosanus* Hayata with water and collecting the cooked solution). Thereafter, a partition is carried out with 25 L of ethyl acetate each time, and then, the upper ethyl acetate layer is removed. A partition with ethyl acetate (25 L) is carried out for another three times, and then, the ethyl acetate layers are incorporated into an ethyl acetate portion, and the lower water layers are also incorporated into a water soluble portion. The water-soluble portion is the extract comprising kinsenoside, and is free of ethyl acetate-philic components. In addition, the water-soluble portion also can be optionally eluted with alcohols (e.g., 10% methanol) to raise the content of kinsenoside.

The extract of *Anoectochilus* spp. can also be used for manufacturing a medicament. The extract of *Anoectochilus* spp. can be used to manufacture a medicament with any suitable forms for inhibiting the activation of macrophages, inhibiting the function of osteoclasts, inhibiting the formation of osteoclasts, and/or activating osteoblasts, and especially can be used for anti-osteoporosis and anti-inflammation (e.g., anti-arthritis).

The present invention will be further illustrated in details with specific examples as follows. After referring to the examples described in the following paragraphs, people skilled in this field can easily appreciate the basic spirit and other invention purposes of the present invention, and technical methods adopted in the present invention and better embodiments. However, the following examples are provided only for illustrating the present invention, and the scope of the present invention is not limited thereby.

[Material]

*Anoectochilus formosanus* Hayata is purchased from Yu-Jung farm in Puli, Taiwan. The specimen of this plant has been stored in the college of Pharmacy, China Medical University, Taiwan, and has been identified by the college (code: CMU AF 0609).

[The Extraction and the Isolation of Kinsenoside]

(1) First, *Anoectochilus formosanus* Hayata (10 kg) was disintegrated in the water (100 L), and the resulting slurry was filtered to obtain a solution (denoted as AFE). This step can be replaced by cooking *Anoectochilus formosanus* Hayata with water, and collecting the solution. Thereafter, a partition was carried out with 25 L of ethyl acetate each time, and then the upper ethyl acetate layer was removed. A partition with ethyl acetate (25 L) was carried out for another three times, and then the ethyl acetate layers were incorporated into an ethyl acetate portion (denoted as AFEE), and the lower water layers were also incorporated into a water-soluble portion (denoted as AFEW).

(2) Under reduced pressure, AFEE and AFEW were evaporated, and a green oil residue (47.4 g) and a red residue (218.4 g) were generated, respectively. The resulting red residue (210 g) from AFEW was placed in a Diaion HP-20 column (Nippon Rensui Co., Japan), and was eluted with water, 10% methanol (in the water), 20% methanol (in the water), 50% methanol (in the water), and 100% methanol, and five partitioned portions (denoted as AFEW-1 to AFEW-5) were obtained. The dry weights of AFEW-1 to AFEW-5 were 141.38 g, 22.06 g, 8.16 g, 9.21 g, and 3.78 g, respectively. The aforesaid operation is shown in FIG. 1.

(3) AFEW-2 (10 g) was further purified by the use of a silica gel column (Si 60 F245, Merck, Germany) and chloroform/ethanol (8:3 to 15:8) was as the mobile phase, and four partitioned portions (denoted as Portion 1 to Portion 4) were obtained. Portion 4 (4.5 g) was collected to be purified with a high performance liquid chromatography (HPLC) instrument, so as to acquire a main active component (4.1 g), which was identified as kinsenoside (i.e. the compound of formula (I)).

The conditions for the HPLC operation are as followings. Pump: Shimadzu LC-8A (Kyoto, Japan); Mobile phase: water; Column: Mightysil ODS RP-18 Aqua column (inner diameter: 20 cm, length: 250 cm, particle size: 5 micrometer, from Kanto Chemical Co., Tokyo, Japan).

The content of the main component in Portion 4 reached 77.6%, and the main component was analyzed with a mass spectrometer (Jeol GCmate, Tokyo, Japan) and a nuclear magnetic resonance (NMR) instrument ($^1$H, $^{13}$C, DEPT, COSY, HMQC, and HMBC, Jeol 400 MHz, Tokyo, Japan), and was identified as kinsenoside (3-(R)-3-β-D-glucopyranosyloxy-butanolide, the compound of the formula (I)). Table 1 shows the NMR data of the isolated kinsenoside.

TABLE 1

$^{13}$C and $^1$H NMR data of kinsenoside (400 MHz, DMSO-$d_6$)

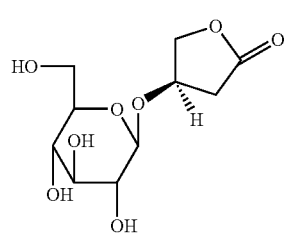

(I)

| $^{13}$C | | $^1$H | |
|---|---|---|---|
| 1 | 175.8 | 2 | 2.87 (dd, 17.8. 6.3) |
| 2 | 34.9 | — | 2.48 (dd, 17.9. 1.3) |
| 3 | 74.3 | 3 | 4.59 (dddd 6.0, 3.6, 2.2, 1.4) |
| 4 | 74.0 | 4 | 4.41 (dd, 10.2. 5.1) |
| | | | 4.38 (dd, 10.3. 1.8) |
| G-1 | 102.1 | G-1 | 4.24 (d, 7.8) |
| G-2 | 73.1 | G-2 | 2.92 (m) |
| G-3 | 76.9 | G-3 | 3.94 (m) |
| G-4 | 69.9 | G-4 | 3.04 (m) |
| G-5 | 76.5 | G-5 | 3.13 (m) |
| G-6 | 61.0 | G-6 | 3.44 (m) |
| | | | 3.66 (dd, 11.7. 5.8) |
| OH2 | | OH2 | 4.9 (d, 4.8) |
| OH3 | | OH3 | 5.0 (d, 5.1) |
| OH4 | | OH4 | 4.8 (d, 5.4) |
| OH6 | | OH6 | 4.5 (t, 5.8) |

Example 1

Kinsenoside Inhibits the Inflammatory Reaction of Macrophages

The inflammatory reaction involves a complicated process including producing radicals (e.g. NO, $H_2O_2$, etc), cytokines (e.g. PGE2, TNF-α, IFN-γ, IL-2, IL-1β, etc), and so on. Therefore, the level of the inflammation reaction can be inferred by measuring the amount of radicals and cytokines relevant to the inflammation reaction in the body.

Experiment A: Kinsenoside Inhibits the Inflammatory Reaction of Macrophages in the Peritoneal Cavity of ICR Mice By means of peritoneal cavity injection, ICR mice (Bio-LASCO, Co., Ltd., Taiwan) were administrated with 5 wt % of thioglycollate (Becton Dickinson, Franklin Lakes, N.J.). After 3 days, macrophages in the peritoneal cavity of the ICR mice were washed out with Hank's Balanced Salt Solutions (Amresco, Solon, Ohio), and were incubated in culture plates (content: Dulbecco's modified eagle's medium, 10% heat-inactivated fetal bovine serum, penicillin (100 U/ml), and streptomycin (100 μg/ml)). Then, kinsenoside (10, 25, 50 μM) was added into the culture plates, and the macrophages were incubated for 30 minutes. Lipopolysaccharides (1 μg/ml, Sigma) were added into the plates to induce the inflammatory reaction of macrophages. 24 hours later, the supernatant was collected, and the content of nitric oxide was determined with a Griess reagent (Sigma). The result is shown in Table 2.

TABLE 2

| Group | kinsenoside concentration (μM) | NO concentration (μM) |
|---|---|---|
| control | 0 | 0.8 ± 0.2 |
| LPS + vehicle | 0 | 32.9 ± 5.5## |
| LPS + kinsenoside | 10 | 26.7 ± 3.2* |
| LPS + kinsenoside | 25 | 20.2 ± 2.1** |
| LPS + kinsenoside | 50 | 16.2 ± 1.0** |

All data are mean ± standard deviation (the number of samples = 3).
Compared to the control group,
$P < 0.05$.
Compared to the LPS + vehicle group,
*$P < 0.05$,
**$P < 0.01$.

Experiment B: Kinsenoside Inhibits the Inflammation Reaction of Macrophages RAW 264.7

Various concentrations (0, 10, 50, and 100 μM) of kinsenoside were added into culture plates (content: Dulbecco's modified eagle's medium, 10% heat-inactivated fetal bovine serum, penicillin (100 U/ml), and streptomycin (100 μg/ml)) containing macrophages RAW 264.7, and after 2 hours, 1 μM of lipopolysaccharides was added. 24 hours later, the supernatant was collected, and the content of nitric oxide was determined with a Griess reagent (Sigma). After macrophages RAW 264.7 were scratched off the culture plates, proteins were extracted, and then the expression of nitric oxide synthase (iNOs), p65, and p50 (nuclear factor kappa B or NF-κB, transcription factor) was analyzed with the western blot method.

Figure 2A:
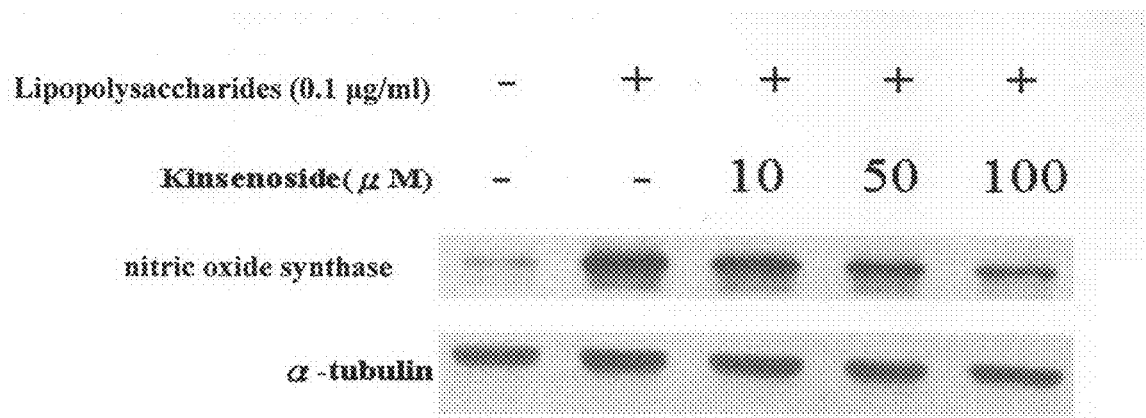
FIG. 2A is a figure of the protein electrophoresis of nitric oxide synthase after the administration of kinsenoside to macrophages RAW 264.7.
Figure 2B:
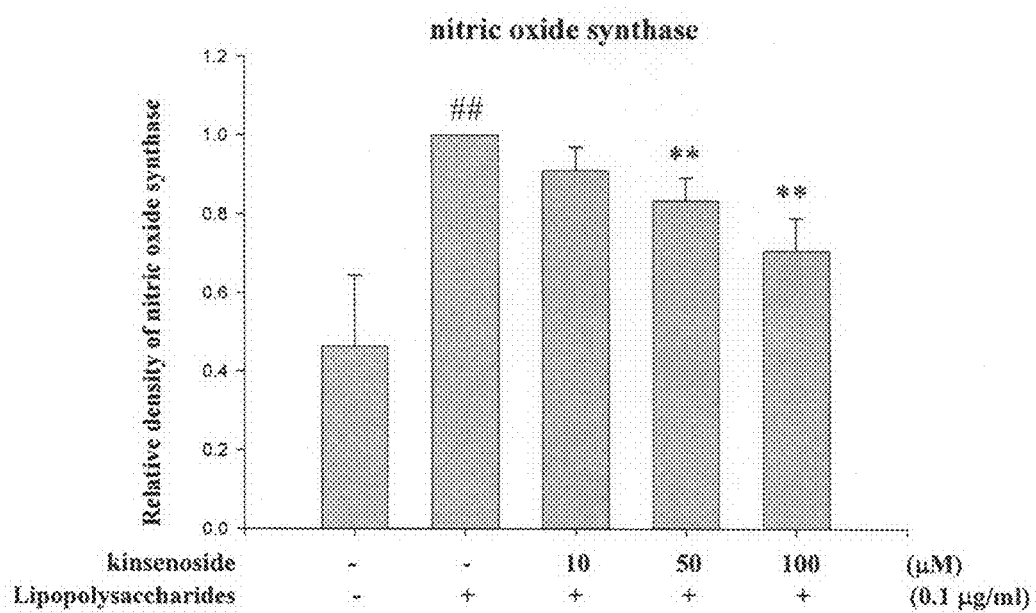
FIG. 2B is a statistic column diagram of nitric oxide synthase after the administration of kinsenoside to macrophages RAW 264.7.
Figure 3A:
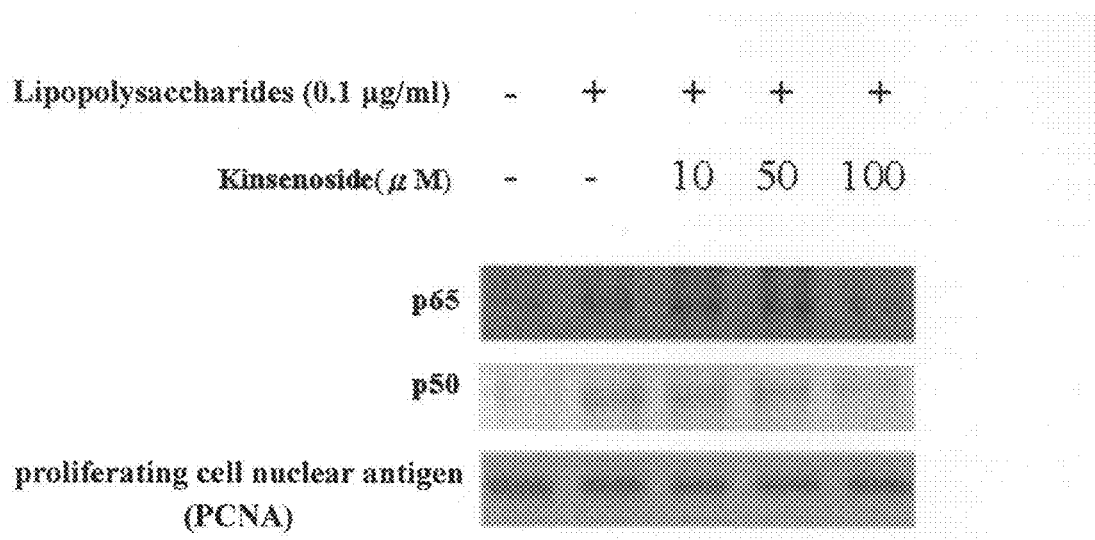
FIG. 3A is a figure of the protein electrophoresis of p65 and p50 proteins in nuclei after the administration of kinsenoside to macrophages RAW 264.7.
Figure 3B:
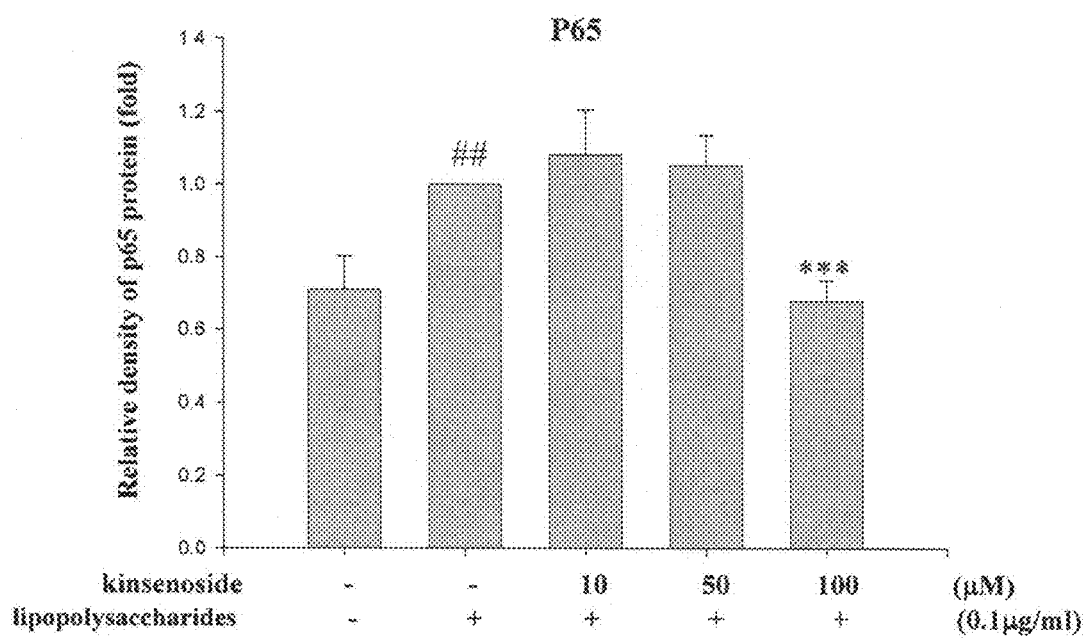
FIG. 3B is a statistic column diagram of p65 protein in nuclei after the administration of kinsenoside to macrophages RAW 264.7.
Figure 3C:
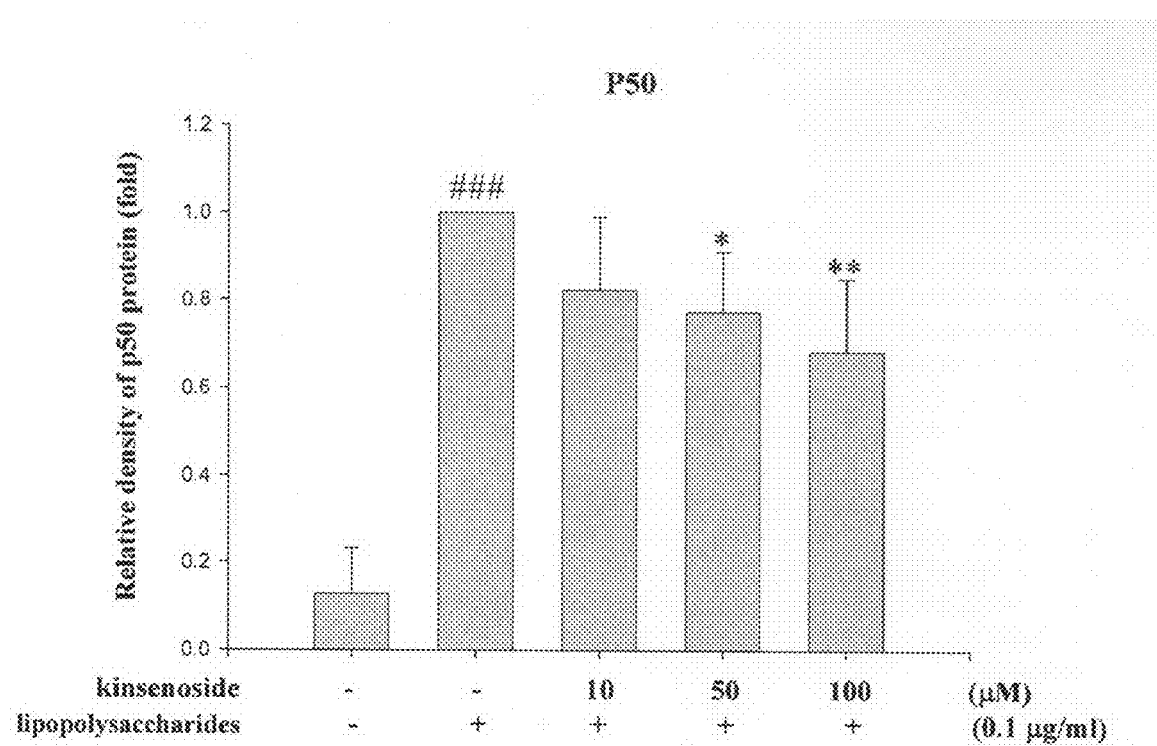
FIG. 3C is a statistic column diagram of p50 protein in nuclei after the administration of kinsenoside to macrophages RAW 264.7.

As shown in Table 3, kinsenoside inhibits the induction activity of lipopolysaccharides toward macrophages to reduce the generation of nitric oxide. FIG. 2A and FIG. 2B shows that kinsenoside inhibits the induction effect of lipopolysaccharides to reduce the expression of nitric oxide synthase. FIG. 3A to FIG. 3C shows that lipopolysaccharides stimulate macrophages RAW 264.7 to make p50 and p65 enter into the nuclei, and this effect can be inhibited by kinsenoside. These results show that kinsenoside can inhibit the inflammation reaction of macrophages via the NF-κB pathway.

TABLE 3

| Group | the concentration of kinsenoside (μM) | the concentration of NO (μM) |
|---|---|---|
| Control | 0 | 1.6 ± 1.5 |
| LPS + water | 0 | 21.0 ± 4.2### |
| LPS + kinsenoside | 10 | 15.5 ± 3.7 |
| LPS + kinsenoside | 50 | 12.0 ± 3.1** |
| LPS + kinsenoside | 100 | 8.4 ± 1.7*** |

All data are mean ± standard deviation (the number of samples = 3).
Compared to the control group, ###$P < 0.001$.
Compared to the LPS + water group, $P < 0.01$, *$P < 0.001$.

Example 2

Kinsenoside Inhibits the Induction Effect of Lipopolysaccharides on the Septicemia of ICR Mice Experiment C: Kinsenoside Inhibits the Induction Effect of Lipopolysaccharides on the Generation of Inflammatory Cytokines in the Blood of ICR Mice ICR mice were intraperitoneally administrated with various dosages (100 mg/kg or 300 mg/kg) of kinsenoside. 30 minutes later, the ICR mice were intraperitoneally administrated with 40 mg/kg of lipopolysaccharides. 1 hour later, the blood of the ICR mice was collected from the retro-orbital sinus, and the concentrations of TNF-α and IL-1β were determined with an ELISA (enzyme linked immunosorbent assay) reagent (eBioscience, Boston, Mass.). The result is shown in Table 4.

TABLE 4

| Group | the dosage of kinsenoside (mg/kg) | TNF-α (ng/ml) | IL-1β (ng/ml) |
|---|---|---|---|
| Control | 0 | 226.9 ± 55.2 | 406.7 ± 69.4 |
| LPS + water | 0 | 1457.7 ± 334.0## | 638.6 ± 163.0# |
| LPS + kinsenoside | 100 | 680.5 ± 160.2* | 371.1 ± 127.8* |
| LPS + kinsenoside | 300 | 513.4 ± 155.0** | 272.6 ± 102.6** |

All data are mean ± standard deviation (the number of samples = 10).
Compared to the control group, #$P < 0.05$, ##$P < 0.01$.
Compared to the LPS + water group, *$P < 0.05$, **$P < 0.01$.

Figure 4:
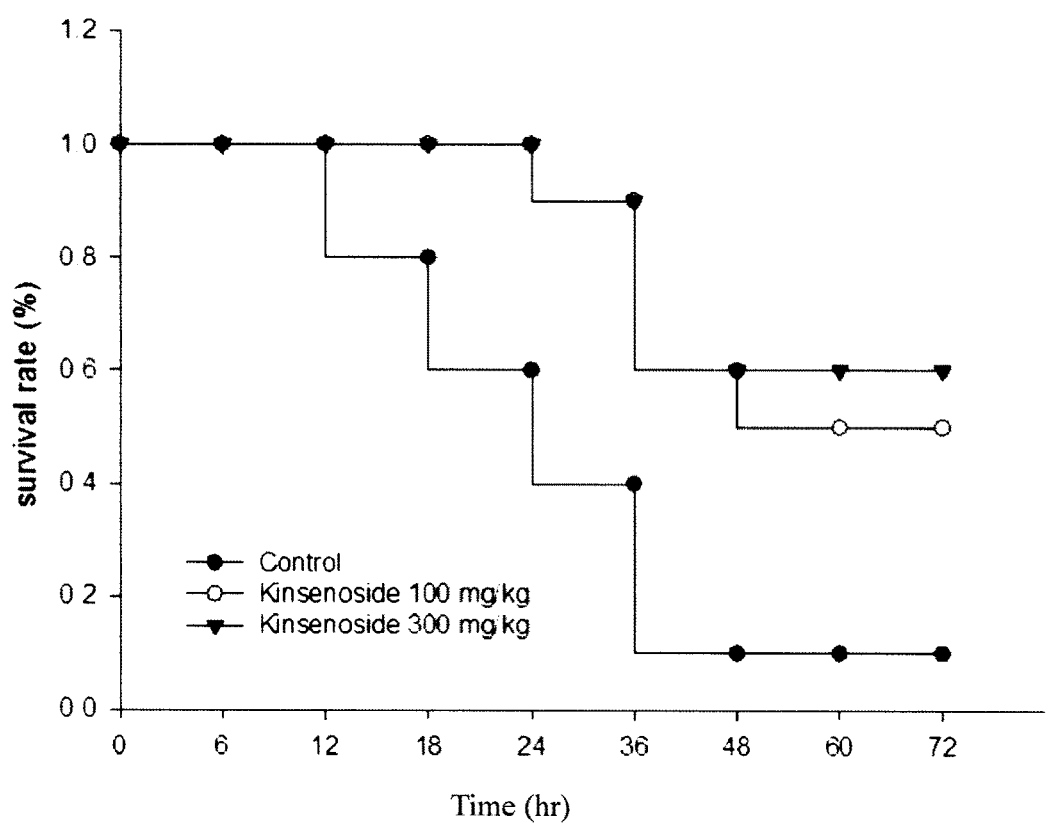
FIG. 4 is a figure illustrating the variation of the death rate of ICR mice after the administration of kinsenoside to the ICR mice.

Experiment D: Kinsenoside Inhibits the Induction Effect of a High Dosage of Lipopolysaccharides on the Septic Shock Death of ICR Mice ICR mice were intraperitoneally administrated with various dosages (100 mg/kg or 300 mg/kg) of kinsenoside. 30 minutes later, the ICR mice were intraperitoneally administrated with 80 mg/kg of lipopolysaccharides, and the death rate of the ICR mice within 72 hours was observed. As shown in FIG. 4, kinsenoside inhibits the death rate of the ICR mice.

As can be seen from Table 2 to Table 4 and from FIG. 2A to FIG. 4, kinsenoside inhibits the induction effect of lipopolysaccharides on the release of nitric oxide from macrophages in the peritoneal cavity of the ICR mice and from macrophages RAW 264.7, and further reduces the induction effect of lipopolysaccharides on the amount of TNF-α and IL-1β in the blood of the ICR mice, so as to efficiently inhibit the death rate of the ICR mice caused by a high dosage of lipopolysaccharides. These results show that kinsenoside may efficiently inhibit the induction effect of lipopolysaccharides on the inflammatory reaction of the ICR mice.

Example 3

Kinsenoside Inhibits the Induction Effect of Collagen on the Rheumatoid Arthritis of BALB/c Mice At the early stage of rheumatoid arthritis, macrophages are activated to release cytokines to cause the inflammation, and at the terminal stage, macrophages differentiate into osteoclasts to cause damage to bones. Hence, rheumatoid arthritis can be cured by inhibiting the activation of macrophages and inhibiting the differentiation from macrophages to osteoclasts.

Experiment E:

BALB/c mice were purchased from the National Laboratory Animal Center, Taiwan. 200 μg of type-IT collagen (Sigma) was subcutaneously injected into the tails of the BALB/c mice to induce the rheumatoid arthritis, wherein type-II collagen was emulsified with a Freund's complete adjuvant (Sigma) previously. At the 215' day, 200 μg of type-II collagen was subcutaneously injected into the tails of the BALB/c mice again, and type-II collagen was emulsified with a Freund's incomplete adjuvant (Sigma) previously. From the day of the second injection, the BALB/c mice were administrated orally with kinsenoside (100 or 300 mg/kg) daily for 21 days. After 21 days, the BALB/c mice were sacrificed, and the blood, inguinal lymph nodes, and soles comprising joints of the BALB/c mice were collected for assay.

The concentrations of TNF-α and antibodies IgE and IgG1 in the serum were determined with ELISA method. Antibodies IgE and IgG1 reagents were purchased form Bethyl, Montgomery, Tex., USA. The results are shown in Table 5 and Table 6.

TABLE 5

| Group | the dosage of kinsenoside (mg/kg) | TNF-α ($10^{-12}$ g/ml) |
| --- | --- | --- |
| control | 0 | 788.3 ± 160.0 |
| collagen + water | 0 | 1281.4 ± 165.4[#] |
| collagen + kinsenoside | 100 | 825.9 ± 155.4* |
| collagen + kinsenoside | 300 | 790.0 ± 194.1* |

All data are mean ± standard deviation (the number of samples = 7).
Compared to the control group, [#]$P < 0.05$.
Compared to the collagen + water group, *$P < 0.05$.

TABLE 6

| Group | the dosage of kinsenoside (mg/kg) | IgE (absorbance) | IgG1 (absorbance) |
| --- | --- | --- | --- |
| control | 0 | 0.06 ± 0.02 | 2.17 ± 0.08 |
| collagen + water | 0 | 0.31 ± 0.09[###] | 2.55 ± 0.07[###] |
| collagen + kinsenoside | 100 | 0.15 ± 0.03*** | 2.44 ± 0.05 |
| collagen + kinsenoside | 300 | 0.13 ± 0.04*** | 2.41 ± 0.10* |

All data are mean ± standard deviation (the number of samples = 7).
Compared to the control group, [###]$P < 0.001$.
Compared to the collagen + water group, *$P < 0.05$, ***$P < 0.001$.

As shown in Table 5, collagen induces arthritis to raise the concentration of TNF-α in the blood of the mice, and kinsenoside inhibits this effect. As shown in Table 6, collagen induces arthritis to raise the amount of antibodies IgE and IgG 1 in the blood of the mice, and kinsenoside also inhibits this effect.

Lymph nodes were taken from the both sides of the groins of the BALB/c mice, and were sieved to produce a single suspended cell line. The number of lymphocytes was determined with a flow cytometer. In addition, B cells and Th2 cells were stained with antibodies CD19/45 and CD4/278 (eBioscience) to obtain the ratio of B cells and Th2 cells. The result is shown in Table 7 and Table 8.

TABLE 7

| Group | the dosage of kinsenoside (mg/kg) | the number of lymphocytes ($10^5$/ml) |
| --- | --- | --- |
| control | 0 | 3.3 ± 0.5 |
| collagen + water | 0 | 4.4 ± 0.9[#] |
| collagen + kinsenoside | 100 | 3.3 ± 0.6* |
| collagen + kinsenoside | 300 | 2.8 ± 1.0*** |

All data are mean ± standard deviation (the number of samples = 7).
Compared to the control group, [#]$P < 0.05$.
Compared to the collagen + water group, *$P < 0.05$, ***$P < 0.001$.

TABLE 8

| Group | the dosage of kinsenoside (mg/kg) | CD19/45 (%) | CD4/278 (%) |
| --- | --- | --- | --- |
| control | 0 | 19.2 ± 3.8 | 5.1 ± 0.7 |
| collagen + water | 0 | 27.0 ± 3.5[##] | 9.1 ± 0.6[###] |
| collagen + kinsenoside | 100 | 19.3 ± 2.1** | 8.0 ± 0.6** |
| collagen + kinsenoside | 300 | 18.6 ± 3.6*** | 7.6 ± 0.6** |

All data are mean ± standard deviation (the number of samples = 7).
Compared to the control group, [##]$P < 0.01$, [###]$P < 0.001$.
Compared to the collagen + water group, $P < 0.01$, *$P < 0.001$.

As shown in Table 7, collagen induces arthritis to increase the number of lymphocytes in the lymph nodes of the groins of the mice, and kinsenoside inhibits this effect. As shown in Table 8, collagen induces arthritis to increase the ratio of B cells and Th2 cells in the lymph nodes of the groins of the mice, and kinsenoside inhibits this effect.

The mRNAs were extracted from the right soles and joints of the mice, and the expression of the mRNAs of TNF-α was analyzed with RT-PCR (Reverse Transcription-Polymerase Chain Reaction). The results are shown in FIG. 5A and FIG. 5B.

Figure 5A:
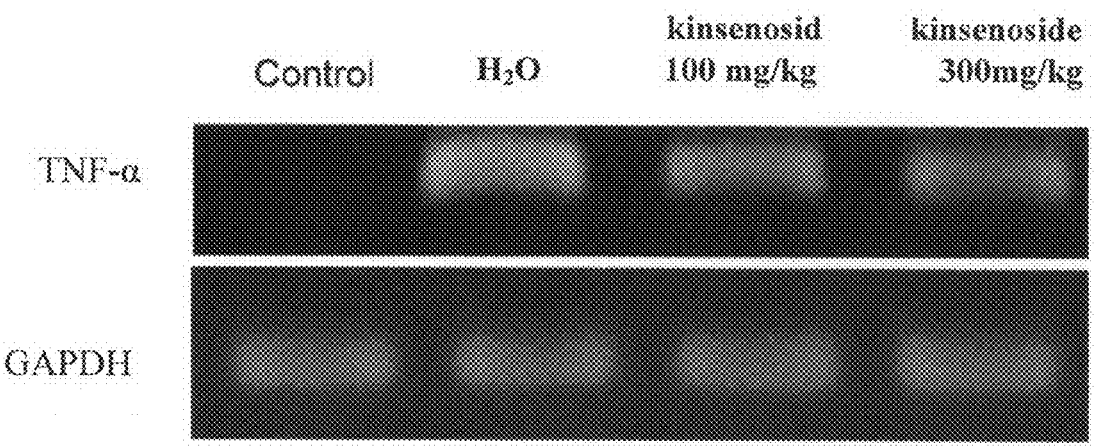
FIG. 5A is a figure of the electrophoresis of mRNA of TNF-α after the administration of kinsenoside to ICR mice with arthritis.
Figure 5B:
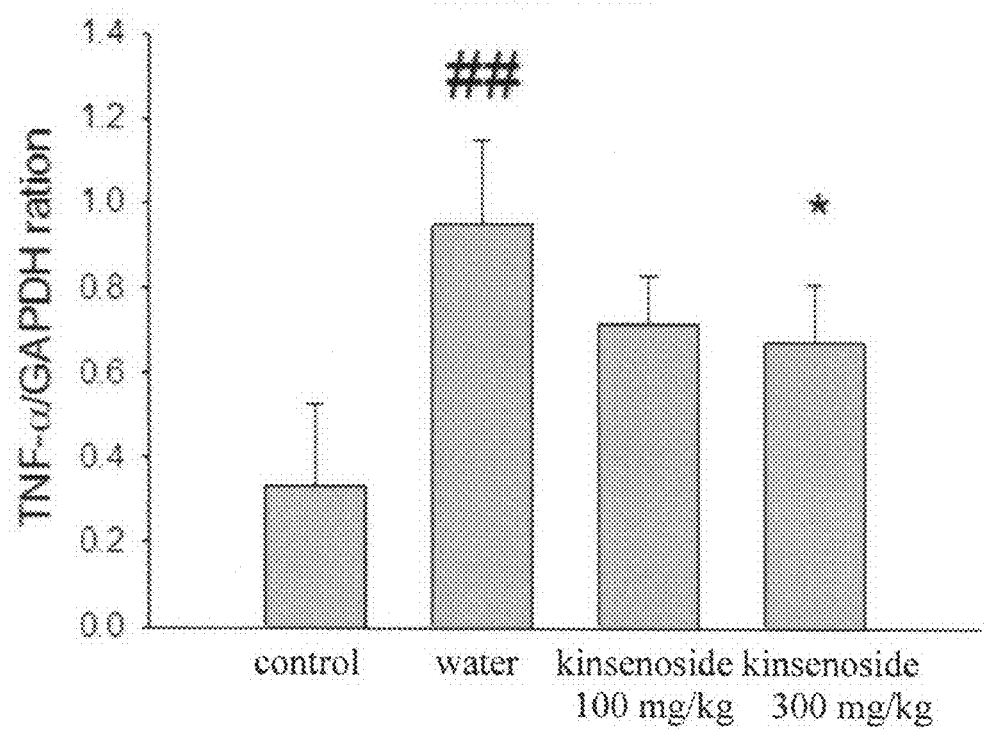
FIG. 5B is a statistic column diagram of mRNA of TNF-α after the administration of kinsenoside to ICR mice with arthritis.

As can be seen from FIG. 5A and FIG. 5B, collagen induces arthritis to ascend the expression of mRNAs of TNF-α in the right soles of the mice, and kinsenoside alleviates the expression of mRNAs of TNF-α.

With respect to rheumatoid arthritis of the mice induced by collagen, kinsenoside can inhibit the release of inflammatory cytokines, and also can reduce the ratio of B cells and Th2 cells in lymphocytes and inhibit the generation of antibodies IgE and IgG2. These results show that kinsenoside may alleviate arthritis caused by collagen, and the anti-inflammation activity of kinsenoside is related to the inhibition effect of kinsenoside on the activation of macrophages and the reduction effect on the antigen-presenting activity of macrophages.

Example 4

Kinsenoside Inhibits the Formation of Osteoclasts

Experiment F: Kinsenoside Inhibits the Formation of Osteoclasts from Myelocytes of Rats Myelocytes were first prepared. Male Wistar rats with the body weight of 250 g to 300 g were used to prepare myelocytes. Under the condition of anaesthesia, the femurs of the rats were taken, and myelocytes were washed out with a phosphate buffer solution. The myelocytes were incubated in culture plates (content: α-minimum essential medium, 10% heat-inactivated fetal bovine serum, penicillin (100 U/ml), and streptomycin (100 µg/ml)), and differentiation inducers, 50 ng/ml of RANKL (receptor for activation of nuclear factor kappa B ligand) (PeproTech EC, London, UK) and 20 ng/ml of M-CSF (macrophage colony stimulating factor) (PeproTech EC, London, UK), that can induce the formation of osteoclasts, were added into the culture plates. After incubation for 9 days, monocytes in the marrow differentiated into osteoclasts. The osteoclasts were stained with a TRAP (tartrate-resistant acid phosphatase) stain reagent (Sigma, Louis, Mo., USA), and the number of the osteoclasts was calculated.

Experimental Group I: with the Addition of Kinsenoside and Estradiol

Besides the same RANKL and M-CSF as the control group, various concentrations (0, 5, 25, 50, and 100 µM) of kinsenoside or 10 nM of estradiol (Wako, Japan) were added into culture plates, respectively. Then, rat myelocytes were incubated for 9 days, and the situation that the myelocytes differentiated into osteoclasts was observed. The percentage of the inhibition effect of kinsenoside and estradiol on the formation of osteoclasts was calculated with the following formula, and the result is shown in Table 9.

Inhibition percentage (%)=(the number of osteoclasts of the control group−the number of osteoclasts of the experimental group)/the number of osteo-clasts of the control group×100%

Experimental Group II: with the Addition of the Inhibitor of Estradiol

In addition to the aforesaid RANKL, kinsenoside, and/or estradiol, the inhibitor of estradiol, Fulvestrant (Sigma, Louis, Mo., USA) (1 nM), was also added into culture plates. Then, rat myelocytes were incubated for 9 days, and the situation that the myelocytes differentiated into osteoclasts was observed. The percentage of the inhibition effect of kinsenoside on the formation of osteoclasts was calculated, and the result is shown in Table 9.

TABLE 9

| Group | the concentration of kinsenoside (μM) | inhibition percentage (%) | |
|---|---|---|---|
| | | Experimental Group I | Experimental Group II |
| control | 0 | 0 | 0 |
| kinsenoside | 5 | 15.3 ± 7.2* | 12.0 ± 7.5 |
| kinsenoside | 25 | 25.0 ± 2.0** | 16.3 ± 6.7 |
| kinsenoside | 50 | 50.3 ± 4.2** | 65.7 ± 3.8 |
| kinsenoside | 100 | 78.1 ± 2.8*** | 76.0 ± 3.6 |
| estradiol | 10 (nM) | 45.7 ± 10.5** | 24.0 ± 13.5[#] |

All data are mean ± standard deviation (the number of samples = 3).
Compared to the control group, *P < 0.05, P < 0.01, *P < 0.001.
Testing with t-test, compared to the estradiol group, [#]P < 0.05.

As can be seen in Table 9, both kinsenoside and estradiol inhibits the formation of osteoclasts. It is known that the insufficiency of estrogen may lead to osteoporosis, and thus estradiol (a kind of estrogen) has been used to cure osteoporosis. Meanwhile, breast cancer has been proved to be relevant to the over secretion of estrogen, and thus a breast cancer patient often needs to take Fulvestrant to inhibit the over secretion of estrogen. Therefore, a patient with both breast cancer and osteoporosis (wherein osteoporosis is not caused by the insufficiency of estrogen) can not be treated with estradiol for curing osteoporosis due to the inhibition effect of Fulvestrant on estradiol. However, as shown in Table 9, Fulvestrant has no inhibition effect on kinsenoside, and thus kinsenoside can be used to treat a breast cancer patient with osteoporosis, and the patient still can take Fulvestrant at the same time.

Experiment G: the Survival Rate Assay for Macrophages RAW 264.7

Experimental Group III: the Effect of Kinsenoside on the Survival Rate of Macrophages RAW 264.7

Various concentrations (0, 10, 25, and 50 μM) of kinsenoside were added into culture plates (content: α-minimum essential medium, 10% heat-inactivated fetal bovine serum, penicillin (100 U/ml), and streptomycin (100 μg/ml)) containing macrophages RAW 264.7 (The Food Industry Research and Development Institute, Taiwan), and the macrophages RAW 264.7 were incubated for 3 days. After 3 days, the survival rate of the macrophages RAW 264.7 was measured with MTS (3-(4,5-di-methylthiazol-2-yl)-5-(3-carboxymethoxyphenyl)-2-(4-sulfophenyl)-2H-tetrazolium) (Promega, Madison, Wis., USA), and the result is shown in Table 10.

Experimental Group IV: the Effect of Kinsenoside on the Survival Rate of Macrophages RAW 264.7 with the Presence of a Differentiation Inducer In addition to the aforesaid various concentrations (0, 10, 25, and 50 μM) of kinsenoside, 50 ng/ml of RANKL was added into culture plates, and macrophages RAW 264.7 were incubated for 3 days. After 3 days, the survival rate of the macrophages RAW 264.7 was measured with MTS, and the result is shown in Table 10.

The mechanism of MTS is that a live cell has the activity of dehydrogenase, so MTS can be reduced to become a red purple soluble product, and the product has the highest absorbance at the wavelength of 490 nm. Therefore, the survival rate of cells can be determined according to the absorbance, and the survival rate of cells can be calculated with the following formula:

Survival rate=the absorbance of the experimental group/the absorbance of the control group×100%

TABLE 10

| | | survival rate (%) | |
|---|---|---|---|
| Group | concentration (μM) | Experimental Group III | Experimental Group IV |
| control | 0 | 100 | 100 |
| kinsenoside | 10 | 117.5 ± 8.0 | 100.3 ± 4.0 |
| kinsenoside | 25 | 139.9 ± 4.9 | 105.0 ± 2.4 |
| kinsenoside | 50 | 136.9 ± 4.8 | 101.0 ± 0.3 |

All data are mean ± standard deviation (the number of samples = 3).

As can be seen in Table 10, kinsenoside or the combination of kinsenoside and RANKL does not influence the survival rate of macrophages RAW 264.7.

Experiment H: Kinsenoside Inhibits the Formation of Osteoclasts from Macrophages RAW 264.7

Figure 6:
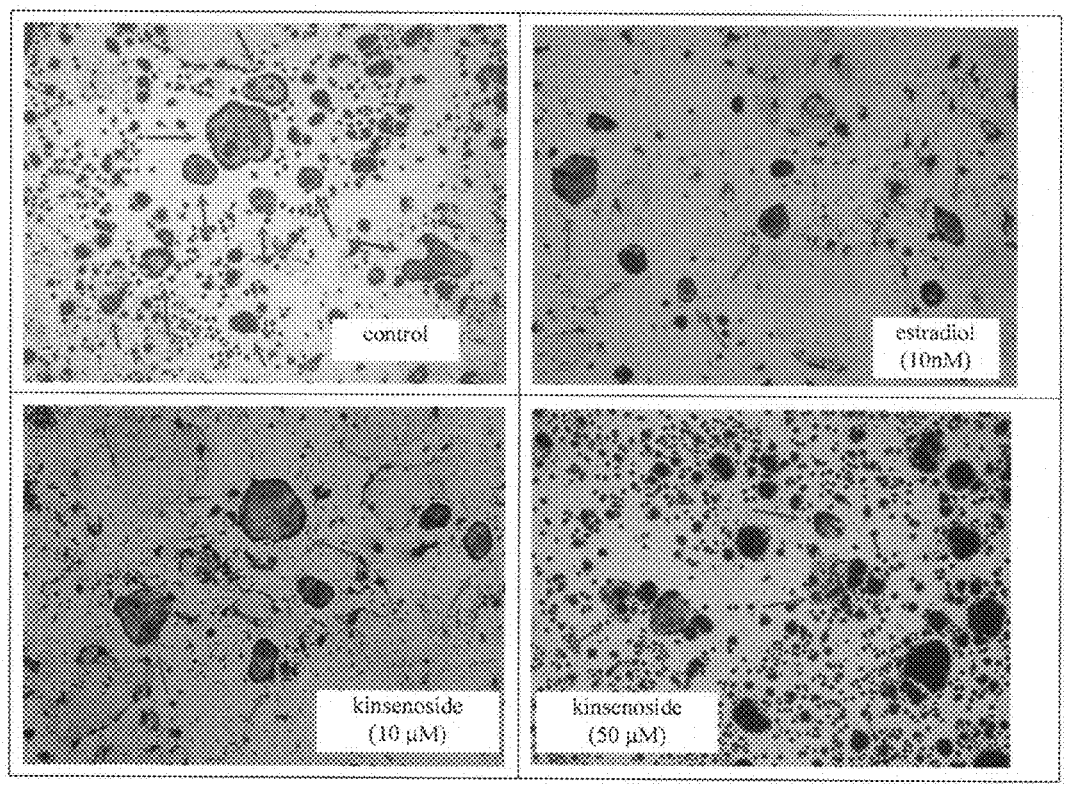
FIG. 6 is microscopic graphs of macrophages RAW 264.7 activated with RANKL after the administration of kinsenoside.

If macrophages RAW 264.7 are incubated in culture plates containing 50 ng/ml of differentiation inducer, RANKL, they usually differentiate into osteoclasts after 5 days. In Experiment H, various concentrations (0, 10, and 50 μM) of kinsenoside or 10 nM of estradiol were added into culture plates containing macrophages RAW 264.7, respectively, and the macrophages RAW 264.7 were incubated for 5 days. After 5 days, osteoclasts were stained with a TRAP stain reagent, and the situation of differentiation was observed with a microscope. The result is shown in FIG. 6. The number of osteoclasts was counted, and the inhibition percentage of the formation of osteoclasts was calculated with the following formula, and the result is shown in Table 11.

Inhibition percentage=(the number of osteoclasts in the control group−the number of osteoclasts in the experimental group)/the number of osteo-clasts in the control group×100%

TABLE 11

| Group | the concentration of kinsenoside (μM) | inhibition percentage (%) |
|---|---|---|
| control | 0 | 0 |
| kinsenoside | 10 | 19 ± 9* |
| kinsenoside | 25 | 59 ± 8** |
| kinsenoside | 50 | 71 ± 3** |
| estradiol | 10 (nM) | 61 ± 16** |

All data are mean ± standard deviation (the number of samples = 3).
Compared to the control group, *P < 0.05, **P < 0.01.

As can be seen from Table II and FIG. 6, with the increase of the concentration of kinsenoside, the inhibition effect of kinsenoside on the formation of osteoclasts from macrophages RAW 264.7 is better (as indicated by the red arrows in FIG. 6). In addition, as shown in Table 10, seeing that kinsenoside or the combination of kinsenoside and RANKL does not influence the survival rate of macrophages RAW 264.7, the mechanism of the inhibition effect of kinsenoside is towards the differentiation of macrophages RAW 264.7, rather than toward the death of macrophages RAW 264.7.

Example 5

Using EMSA to Analyze the Mechanism of the Inhibition Effect of Kinsenoside on the Formation of Osteoclasts Experiment I: the Relationship Between RANKL Stimulation Time and Response EMSA (Electrophoresis Mobility Shift Assay) was used to observe the mechanism of the inhibition effect of kinsenoside on the formation of osteoclasts. It is known that RANKL may activate macrophages RAW 264.7 to make NF-κB enter nuclei to stimulate macrophages RAW 264.7 to differentiate into osteoclasts (see Wada T, Nakashima T, Hiroshi N, Penninger J M. 2006. RANKL-RANK signaling in osteoclastogenesis and bone disease. *Trends Mol. Med.* 12, 17-25).

50 ng/ml of RANKL was added into culture plates containing macrophages RAW 264.7, and the macrophages RAW 264.7 were incubated for 0, 15, 30, 60, and 120 minutes, and then proteins in the nuclei were extracted respectively to be analyzed with EMSA. The result is shown in FIG. 7A. The DNA sequences used in the EMSA assay are as follows:

(SEQ ID NO: 1)
cy5-5'-TCGACCAACTGGGGACTCTCCCTTTGGGAACA-3'

(SEQ ID NO: 2)
cy5-5'-TCGATGTTCCCAAAGGGAGAGTCCCCAGTTGG-3'.

As can be seen from FIG. 7A, with respect to macrophages RAW 264.7 stimulated with RANKL, the amount of NF-κB that entered into the nuclei reached a maximum after 60 minutes. Thus, according to this result, the time of 60 minutes was used as the measure time for RANKL stimulation response in the next experiment.

Experiment J: Kinsenoside Reduces the Amount of NF-κB that Entered into Nuclei 50 ng/ml of RANKL was added into culture plates containing macrophages RAW 264.7, and then various concentrations (0, 10, 25, and 50 μM) of kinsenoside were added thereto, respectively. The macrophages RAW 264.7 were incubated for 60 minutes, and then proteins in the nuclei were extracted to be analyzed with EMSA. The result is shown in FIG. 7B and FIG. 7C. Herein, the DNA sequences used in the EMSA assay are the same as the above experiment. As can be seen from FIG. 7B and FIG. 7C, kinsenoside reduces the amount of NF-κB that enters into the nuclei.

As can be seen from the above description, kinsenoside may reduce the amount of NF-κB that enters into nuclei in macrophages RAW 264.7 to inhibit the formation of osteoclasts from macrophages RAW 264.7. On the basis of this mechanism, the pharmaceutical composition or the extract comprising kinsenoside has the effect of inhibiting bone resorption.

Example 6

Kinsenoside Inhibits the Activity of Osteoclasts

As osteoclasts are activated, they RELEASE MMP-9 (metalloproteinases 9) to erode collagen in bones. Using RT-PCR to analyze the expression of mRNA of MMP-9, one can see if kinsenoside inhibits the bone resorption activity of osteoclasts.

Figure 8A:
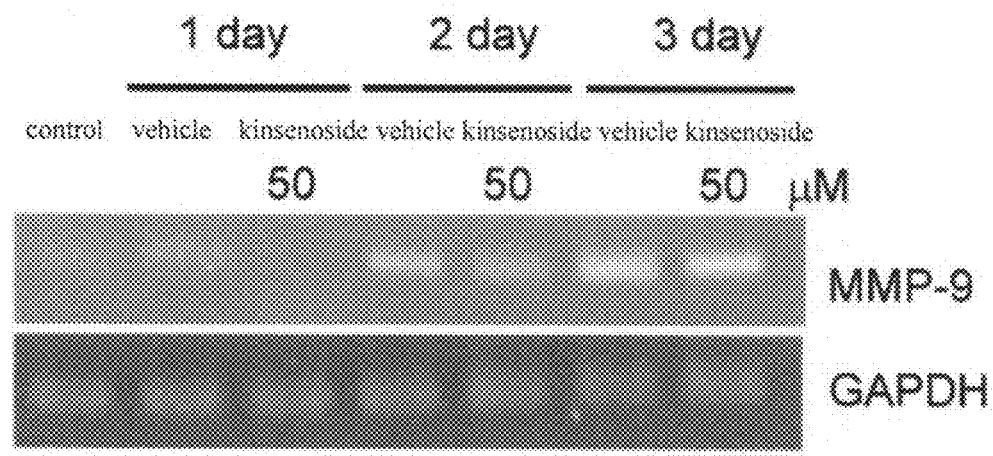
FIG. 8A is a figure of the electrophoresis of mRNA of metalloproteinases 9 (MMP-9) after the administration of kinsenoside to macrophages RAW 264.7.
Figure 8B:
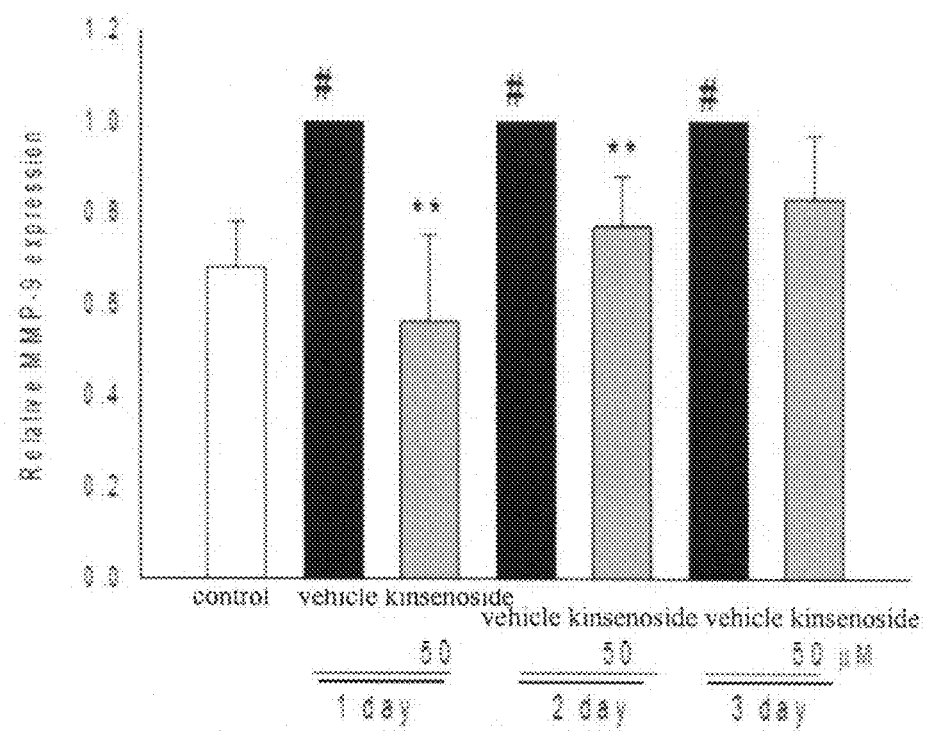
FIG. 8B is a statistic column diagram of mRNA of MMP-9 after the administration of kinsenoside to macrophages RAW 264.7.

Experiment K: Kinsenoside Inhibits the Expression of mRNA of MMP-9 in Osteoclasts As macrophages RAW 264.7 were incubated in culture plates containing 50 ng/ml of RANKL, 50 μM of kinsenoside was added thereto. After the macrophages RAW 264.7 were incubated for 24, 48, and 72 hours, mRNAs were extracted to analyze the expression of MMP-9 with RT-PCR. The result is shown in FIG. 8A and FIG. 8B. Kinsenoside inhibits the expression of mRNA of MMP-9 in osteoclasts. Thus, kinsenoside can inhibit the bone resorption of osteoclasts.

Example 7

Kinsenoside Activates Osteoblasts

Experiment L: the Effect of Kinsenoside on the Survival Rate of the Precursor Cells of Osteoblasts, MC3T3-E1

Experimental Group V: the Effect of Kinsenoside on the Survival Rate of MC3T3-E1 Cells MC3T3-E1 cells (American Type Culture Collection, Manassas, Va., USA) are the precursor cells of osteoblasts. A suitable differentiation inducer can be added into culture plates containing MC3T3-E1 cells to observe the later stage of the differentiation process of osteoblasts. Various concentrations (0, 100, and 1,000 nM) of kinsenoside were added into culture plates (content: α-minimum essential medium, 10% heat-inactivated fetal bovine serum, penicillin (100 U/ml), and streptomycin (100 μg/ml)) containing MC3T3-E1 cells respectively, and the MC3T3-E1 cells were incubated for 3 days. After 3 days, the survival rate of the MC3T3-E1 cells was determined with MTS, and the result is shown in Table 12.

Experimental Group VI: the Effect of Kinsenoside on the Survival Rate of MC3T3-E1 Cells with the Presence of a Differentiation Inducer Besides various concentrations of kinsenoside as the above experiment, 50 μg/ml of Vitamin C (Sigma) and 10 μM of β-glycerophosphatase (Sigma) as differentiation inducers were added into culture plates containing MC3T3-E1 cells, and the MC3T3-E1 cells were incubated for 3 days. After 3 days, the survival rate of the MC3T3-E1 cells was determined with MTS, and the result is shown in Table 12. The cell survival rate is calculated with the following formula:

Survival rate=the absorbance of the experimental group/the absorbance of the control group×100%

TABLE 12

| Group | the concentration of kinsenoside (nM) | survival rate (%) | |
|---|---|---|---|
| | | Experimental Group V | Experimental Group VI |
| control | 0 | 100 | 100 |
| kinsenoside | 10 | 91.5 ± 3.0* | 98.7 ± 7.8 |
| kinsenoside | 100 | 90.8 ± 2.9* | 95.3 ± 3.3 |
| kinsenoside | 1000 | 89.5 ± 6.0** | 95.0 ± 4.5 |

All data are mean ± standard deviation (the number of samples = 3).
Compared to the control group, *P < 0.05, **P < 0.01.

As can be seen from Table 12, although kinsenoside alone slightly decreases the survival rate of the MC3T3-E1 cells, the combination of kinsenoside, Vitamin C, and β-glycerophosphatase does not influence the survival rate of the MC3T3-E1 cells.

Experiment M: Kinsenoside Stimulates MC3T3-E1 Cells to Release Alkaline Phosphatase ALP (alkaline phosphatase) is a molecular indicator or molecular marker for the early stage of the activation of the precursor cells of osteoblasts, and according to the activity of ALP, the activation situation of the precursor cells of osteoblasts can observed. First, 50 μg/ml of Vitamin C and 10 mM of β-glycerophosphatase were added into culture plates containing MC3T3-E1 cells, and various concentrations (0, 100, and 1,000 nM) of kinsenoside were added into the culture plates, respectively. The MC3T3-E1 cells were incubated for 3, 5, and 10 days respectively, and then proteins in the cells were extracted. A p-nitrophenyl phosphate liquid substrate system reagent (Sigma) was used to determine the activity of ALP, and the result is shown in Table 13.

TABLE 13

| Group | the concentration of kinsenoside (nM) | ALP activity (%) | | |
|---|---|---|---|---|
| | | 3 days | 5 days | 10 days |
| control | 0 | 100 | 100 | 100 |
| kinsenoside | 10 | 112 ± 11 | 120 ± 18 | 125 ± 6 |
| kinsenoside | 100 | 124 ± 17 | 126 ± 17 | 137 ± 16 |
| kinsenoside | 1000 | 130 ± 21 | 132 ± 16* | 150 ± 23* |

All data are mean ± standard deviation (the number of samples = 3).
Compared to the control group, *P < 0.05.

As can be seen from Table 13, with the increase of time, kinsenoside enhances the activity of ALP to about 25% to 50%. That is, kinsenoside stimulates MC3T3-E1 cells to differentiate into osteoblasts by activating related enzymes (e.g. ALP) in MC3T3-E1 cells.

Experiment N: Kinsenoside Stimulates MC3T3-E1 Cells to Mineralize

50 μg/ml of Vitamin C and 10 μM of β-glycerophosphatase were added into culture plates containing MC3T3-E1 cells, and the MC3T3-E1 cells were incubated for 14 days. After 14 days, the mineralization of the MC3T3-E1 cells occurred, and led to the deposition of calcium. Alizarin red-S (Sigma) was used to measure the content of calcium (see Gregory C A, Gunn W G, Peister A, Prockop D J. 2004. An Alizarin red-based assay of mineralization by adherent cells in culture: comparison with cetylpyridinium chloride extract. Anal. Biochem. 329, 77-84).

Figure 9:
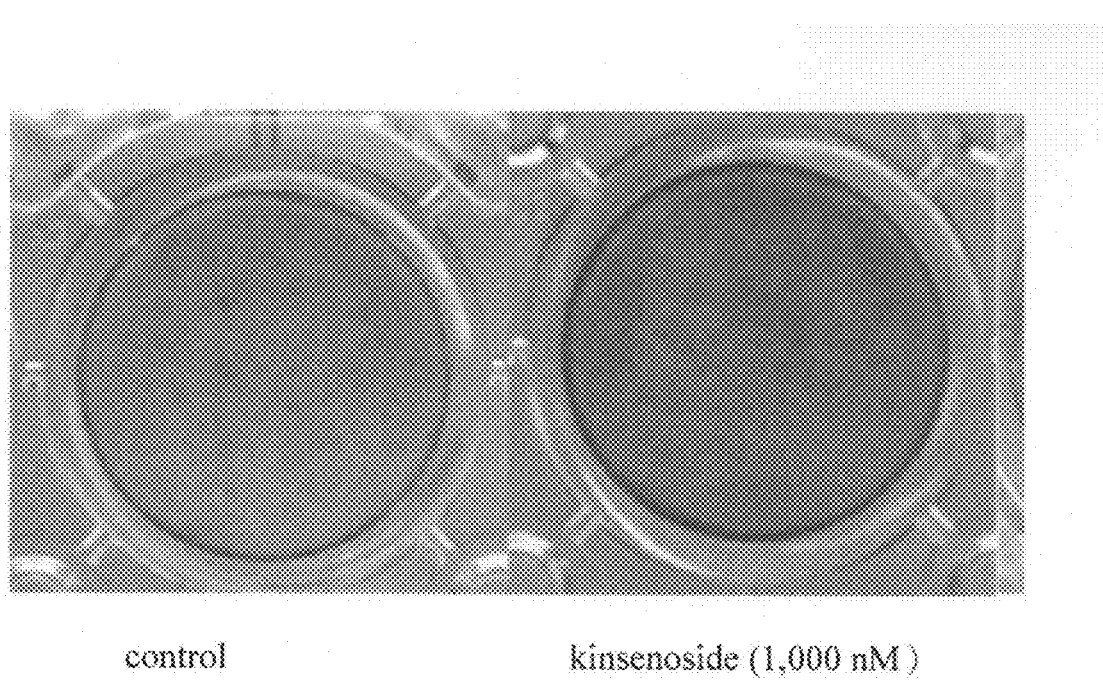
FIG. 9 illustrates the stained culture plates of MC3T3-E1 cells after the administration of kinsenoside to MC3T3-E1 cells.

50 μg/ml of Vitamin C and 10 μM of 0-glycerophosphatase were added into culture plates containing MC3T3-E1 cells, and various concentrations (0, 100, and 1,000 nM) of kinsenoside were added into the culture plates, respectively. The MC3T3-E1 cells were incubated for 14 days, and Alizarin red-S was used to measure the content of calcium. The result is shown in Table 14, and the appearance of the culture plates after staining is shown in FIG. 9.

TABLE 14

| Group | the concentration of kinsenoside (nM) | Alizarin red-S (%) |
|---|---|---|
| control | 0 | 100 |
| kinsenoside | 10 | 137 ± 29 |
| kinsenoside | 100 | 137 ± 27 |
| kinsenoside | 1000 | 174 ± 42* |

All data are mean ± standard deviation (the number of samples = 3).
Compared to the control group, *P < 0.05.

As can be seen from Table 14 and FIG. 9, kinsenoside raises the absorbance of Alizarin red-S. That is, kinsenoside increases the content of calcium in the MC3T3-E1 cells to stimulate the mineralization of the MC3T3-E1 cells.

Example 8

Kinsenoside Improves the Osteoporosis of Ovariectomized Mice

As described above, it is known that the insufficiency of estrogen may cause osteoporosis. Thus, in this experiment, the ovaries of ICR mice were removed to disable the secretion of estrogen to induce osteoporosis.

Figure 10:
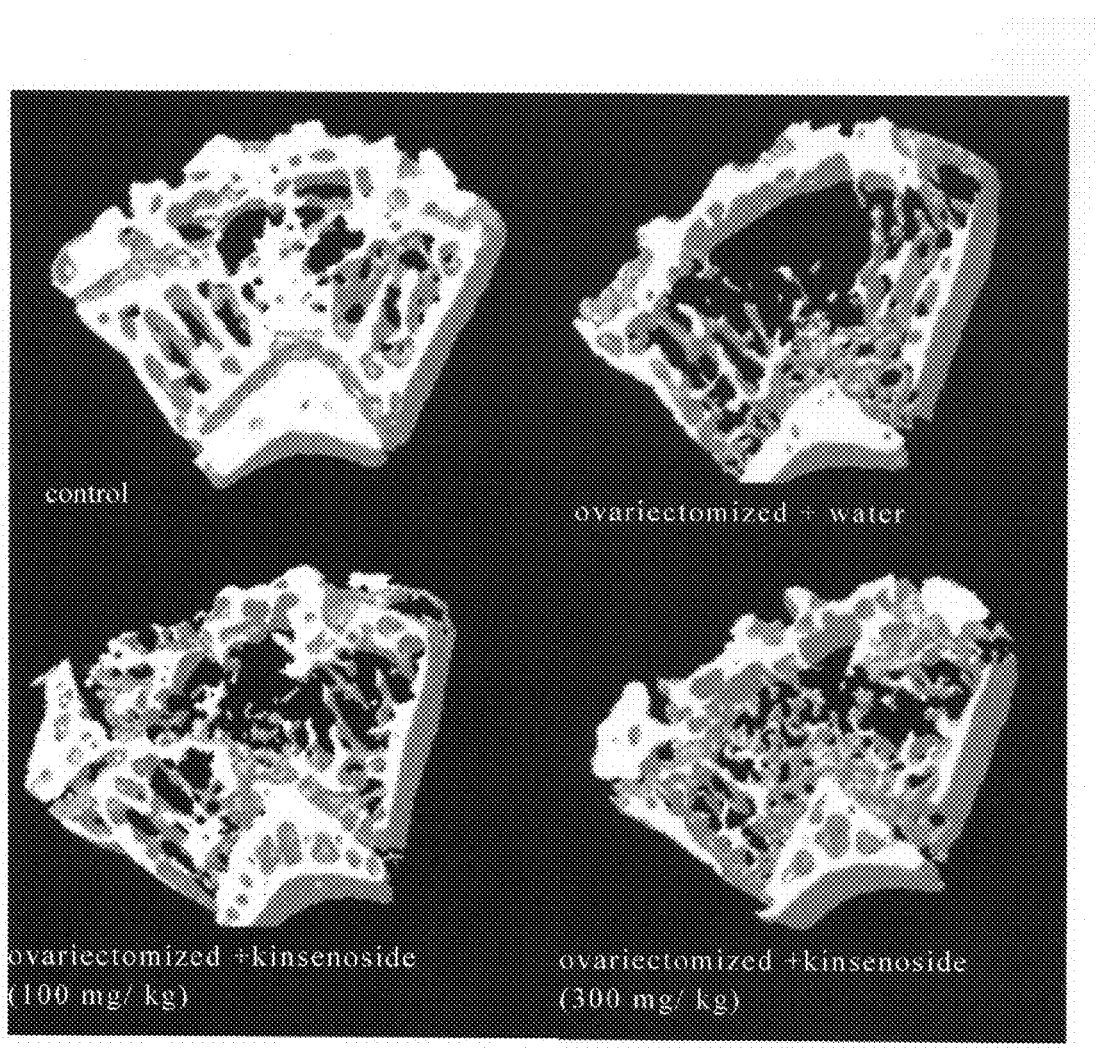
FIG. 10 illustrates the micro computed tomography of the femur epiphysis portion of ovariectomized ICR mice after the administration of kinsenoside to the ovariectomized ICR mice.
Figure 11:
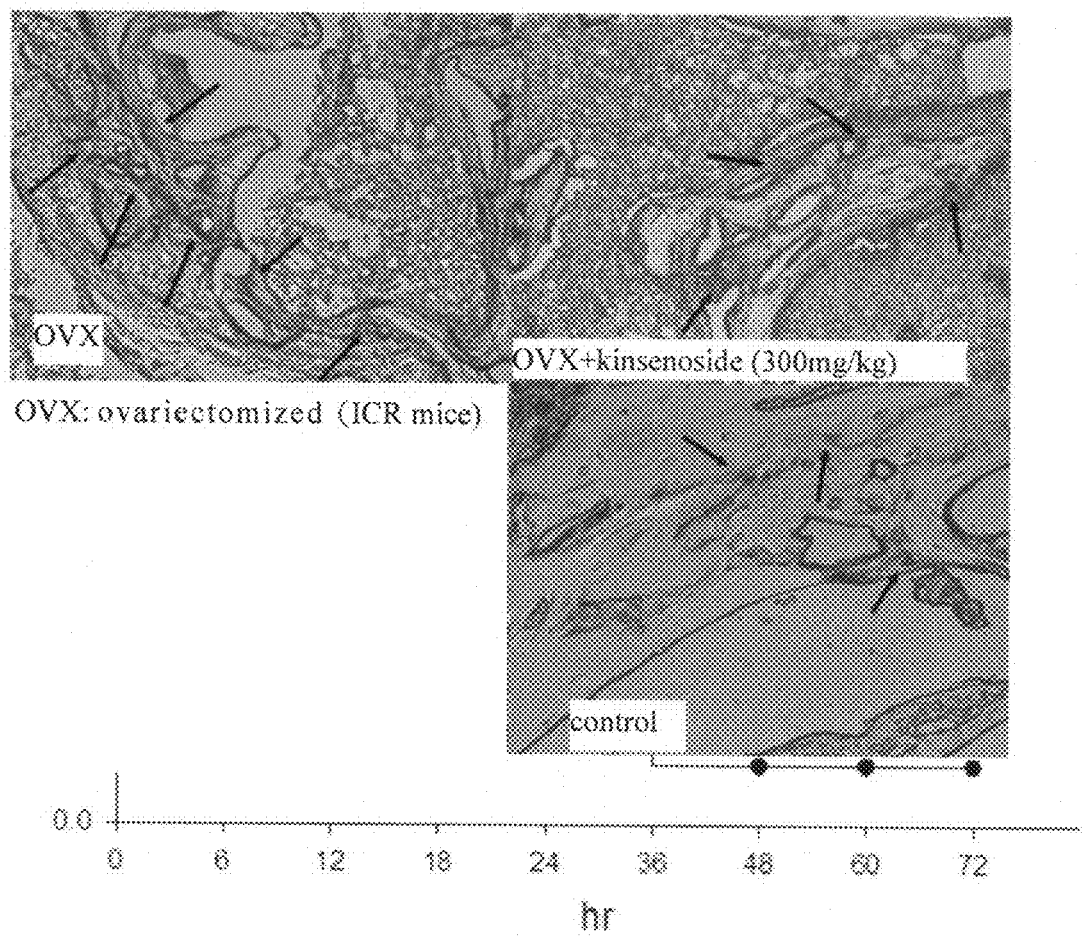
FIG. 11 illustrates microscopic graphs of osteoclasts around the femur trabecula after the administration of kinsenoside to ovariectomized ICR mice.

First, the ovaries of ICR mice were removed. After 3 days, the ICR mice were administrated with various dosages (0, 100, and 300 mg/kg) of kinsenoside, respectively. Herein, the unit "mg/kg" means that the dosage (mg) required for each kilogram of the body weight of an animal. After 3 weeks, the ICR mice were sacrificed. ELISA was used to determine the content of osteocalcin and C-terminal cross-lined telopeptides of type I collagen (CTx) in serum. The reagents for determining osteocalcin and CTx were purchased from IDS Nordic A/S, Herlev, Danmarkids. The result is shown in Table 15. The femurs of the sacrificed ICR mice were taken, and were photographed by a micro computed tomography (Sky-Scan 1076, Kontizh, Belgium). The computerized axial tomography is shown in FIG. 10, and the ratio of bone volume to tissue volume and the number of trabecula were analyzed with analysis software. The result is shown in Table 16. Then, the femurs were decalcified and were frozen sectioned. Osteoclasts in the femurs were stained with a TRAP stain reagent. The number of osteoclasts around the trabecula was counted, and the result is shown in FIG. 11 and Table 17.

TABLE 15

| Group | the dosage of kinsenoside (mg/kg) | CTx (ng/ml) | osteocalcin (ng/ml) |
|---|---|---|---|
| control | 0 | 24.4 ± 3.4 | 82.2 ± 10.9 |
| OVX + water | 0 | 36.9 ± 5.2### | 137.5 ± 19.8## |
| OVX + kinsenoside | 100 | 29.7 ± 6.9* | 191.2 ± 33.5 |
| OVX + kinsenoside | 300 | 27.5 ± 3.1** | 351.8 ± 80.5*** |

All data are mean ± standard deviation (the number of samples = 7).
"OVX" represents ovariectomized mice.
Compared to the control group, ##P < 0.05, ###P < 0.001.
Compared to the OVX + water group, *P < 0.05, P < 0.01, *P < 0.001.

As shown in Table 15, the concentration of CTx in the blood of the ovariectomized ICR mice is increased, and the concentration of osteocalcin is also increased. CTx is a breakdown product of collagen in bones. If the concentration of CTx in the blood is increased, it represents the increase of the bone resorption. Osteocalcin is a small protein generated by osteoblasts. If the concentration of osteocalcin is increased, it represents the increase of the activity of the bone formation or the increase of bone turnover rate (see Swaminathan R. 2001. Biochemical markers of bone turnover. *Clinica Chimica Acta* 313, 95-105). As can be seen in Table 15, kinsenoside decreases the concentration of CTx and increases the concentration of osteocalcin. Thus, kinsenoside can inhibit osteoclasts and increase the activity of osteoblasts or bone turnover rate.

TABLE 16

| Group | the dosage of kinsenoside (mg/kg) | bone volume/tissue volume (%) | the number of trabecula (/cm) |
|---|---|---|---|
| control | 0 | 27.6 ± 2.6 | 12.4 ± 2.2 |
| OVX + water | 0 | 17.2 ± 1.8### | 9.0 ± 1.8## |
| OVX + kinsenosdie | 100 | 19.9 ± 1.5* | 12.2 ± 1.5* |
| OVX + kinsenoside | 300 | 21.2 ± 2.2* | 12.8 ± 1.5* |

All data are mean ± standard deviation (the number of samples = 7).
"OVX" represents ovariectomized mice.
Compared to the control group, ##$p < 0.05$, ###$p < 0.001$.
Compared to the OVX + water group, *$p < 0.05$.

As can be seen from Table 16, kinsenoside increases the ratio of bone volume to tissue volume and the number of trabecula in the ovariectomized ICR mice. Kinsenoside efficiently improves the osteoporosis of the ovariectomized ICR mice, and makes the number of trabecula return to a normal state (compared to the ICR mice that are not ovariectomized). In addition, as shown in FIG. 10, compared to the ICR mice that are not ovariectomized, the micro computed tomography shows that kinsenoside makes the bone tissues of the femurs of the ICR mice return to a normal state.

TABLE 17

| Group | the dosage of kinsenoside (mg/kg) | the number of osteoclasts/bone surface (mm) |
|---|---|---|
| Control | 0 | 3.2 ± 0.4 |
| OVX + water | 0 | 6.6 ± 1.0## |
| OVX + kinsenoside | 100 | 5.7 ± 0.9* |
| OVX + kinsenoside | 300 | 4.3 ± 0.8** |

All data are mean ± standard deviation (the number of samples = 7).
"OVX" represents ovariectomized mice.
Compared to the control group, ##$p < 0.05$.
Compared to the OVX + water group, *$p < 0.05$, **$p < 0.01$.

FIG. 11 and Table 17 are the microscopic graph and the statistic table of the osteoclasts of the ovariectomized ICR mice in this experiment, respectively, and the osteoclasts are around the trabecula of the femurs of the ICR mice. As indicated by the black arrows in FIG. 11, kinsenoside efficiently decreases the number and the density of the osteoclasts in the ovariectomized ICR mice.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can make various changes and modifications of the invention to adapt it to various usages and conditions without departing from the spirit and scope thereof. Therefore, the scope of protection of the subject invention is substantially covered in the following claims as appended.

What is claimed is:

1. A method for inhibiting the activation of macrophages, inhibiting the function of osteoclasts, inhibiting the formation of osteoclasts, and/or activating osteoblasts in a mammal comprising administrating an effective amount of a compound of formula (I) or a pharmaceutically acceptable salt or ester thereof to the mammal:

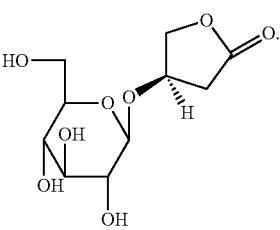

2. The method as claimed in claim 1, wherein the compound of formula (I) is from *Anoectochilus* spp.

3. The method as claimed in claim 2, wherein the *Anoectochilus* spp. is *Anoectochilus formosanus* Hayata.

4. The method as claimed in claim 1, which is for anti-osteoporosis.

5. The method as claimed in claim 1, which is for anti-inflammation.

6. The method as claimed in claim 5, which is for anti-rheumatoid arthritis, anti-gouty arthritis, anti-bacterial arthritis, anti-degenerative arthritis, anti-ankylosing arthritis, or anti-osteoarthritis.

7. The method as claimed in claim 1, wherein the compound of formula (I) or a pharmaceutically acceptable salt or ester thereof is administered as a pharmaceutical composition.

8. The method as claimed in claim 7, wherein the method is for anti-osteoporosis and the amount of the compound of formula (I) or the pharmaceutically acceptable salt or ester thereof, calculated as the compound of formula (I), is about 4 wt % to about 8 wt %, based on the total weight of the composition.

9. The method as claimed in claim 7, wherein the method is for anti-inflammation and the amount of the compound of formula (I) or the pharmaceutically acceptable salt or ester thereof, calculated as the compound of formula (I), is about 7 wt % to about 13 wt %, based on the total weight of the composition.

10. The method as claimed in claim 1, wherein the compound of formula (I) is administrated as an *Anoectochilus* spp. extract.

11. The method as claimed in claim 10, wherein the extract is an aqueous extract.

12. The method as claimed in claim 10, wherein the extract is substantially free of ethyl acetate-philic components.

\* \* \* \* \*

SEQUENCE LISTING

<160> NUMBER OF SEQ ID NOS: 2

<210> SEQ ID NO 1
<211> LENGTH: 32
<212> TYPE: DNA
<213> ORGANISM: Mouse

<400> SEQUENCE: 1
tcgaccaact ggggactctc cctttgggaa ca                    32

<210> SEQ ID NO 2
<211> LENGTH: 32
<212> TYPE: DNA
<213> ORGANISM: Mouse

<400> SEQUENCE: 2
tcgatgttcc caaagggaga gtccccagtt gg                    32